(12) United States Patent
Coutte et al.

(10) Patent No.: US 9,688,725 B2
(45) Date of Patent: Jun. 27, 2017

(54) BACILLUS SP. BIOSURFACTANTS, COMPOSITION INCLUDING SAME, METHOD FOR OBTAINING SAME, AND USE THEREOF

(71) Applicant: Universite Lille 1—Sciences ET Technologies—USTL, Villeneuve-d'Ascq Cedex (FR)

(72) Inventors: Francois Coutte, Lille (FR); Philippe Jacques, Liege (BE); Didier Lecouturier, Chereng (FR); Jean-Sebastien Guez, Veyre-Monton (FR); Pascal Dhulster, Lille (FR); Valerie Leclere, Villeneuve-d'Ascq (FR); Max Bechet, Villeneuve-d'Ascq (FR)

(73) Assignee: Universite Lille 1—Sciences Et Technologies—USTL, Villeneuve-D'Ascq (FR)

( * ) Notice: Subject to any disclaimer, the term of this patent is extended or adjusted under 35 U.S.C. 154(b) by 145 days.

(21) Appl. No.: 14/349,130

(22) PCT Filed: Oct. 3, 2012

(86) PCT No.: PCT/FR2012/052234
§ 371 (c)(1),
(2) Date: Apr. 2, 2014

(87) PCT Pub. No.: WO2013/050700
PCT Pub. Date: Apr. 11, 2013

(65) Prior Publication Data
US 2015/0045290 A1 Feb. 12, 2015

(30) Foreign Application Priority Data
Oct. 3, 2011 (FR) ...................................... 11 58922

(51) Int. Cl.
| | | |
|---|---|---|
| *C07K 7/64* | (2006.01) | |
| *A01N 37/18* | (2006.01) | |
| *C07K 14/32* | (2006.01) | |
| *C12P 21/02* | (2006.01) | |
| *C12M 1/00* | (2006.01) | |
| *A01N 43/36* | (2006.01) | |

(52) U.S. Cl.
CPC .............. *C07K 7/64* (2013.01); *A01N 43/36* (2013.01); *C07K 14/32* (2013.01); *C12M 47/10* (2013.01); *C12P 21/02* (2013.01)

(58) Field of Classification Search
CPC ... C07K 7/52; C07K 7/54; C07K 7/56; C07K 7/64
See application file for complete search history.

(56) References Cited

U.S. PATENT DOCUMENTS 6,638,910 B2 10/2003 Heins et al.
7,011,969 B2 3/2006 Yoneda et al.

FOREIGN PATENT DOCUMENTS

| CZ | 20011620 A3 | 9/2001 |
|---|---|---|
| EP | 1320595 A2 | 6/2003 |
| WO | 0226961 A2 | 4/2002 |

OTHER PUBLICATIONS

T. Stein. "Whole-cell matrix-assisted laser desorption/ionization mass spectrometry for rapid identification of bacteriocin/lantibiotic-producing bacteria", Rapid Commun. Mass Spectrom. 22:1146-1152. (2008).*
Bacillus subtilis entry in Wikipedia. Retrieved from "https://en.wikipedia.org/w/index.php?title=Bacillus_subtilis &oldid=733967707" on Aug. 15, 2016.*
Patrick Fickers et al.; High-Level Biosynthesis of the Anteiso-C17 Isoform of the Antibiotic Mycosubtilin in Bacillus subtilis and Characterization of Its Candidacidal Activity; Applied and Environmental Microbiology, vol. 75, No. 13, Jul. 2009 (Jul. 2009), pp. 4636-4640, XP002707276, pp. 4636-4640.
Valerie Leclere et al.; Mycosubtilin Overproduction by Bacillus subtillis BBG100 Enhances the Organism's Antagonistic and Biocontrol Activities; Applied and Environmental Microbiology, vol. 71, No. 8, Aug. 1, 2005, pp. 4577-4584, XP055046643, ISSN:0099-2240, DOI: 10.1128/AEM.71.8.4577-4584.2005.
Francois Coutte et al.; Production of surfactin and fengycin by Bacillus subtilis in a bubbleless membrane bioreactor; Applied Microbiology and Biotechnology, Springer, Berlin, DE, vol. 87, No. 2, Mar. 11, 2010, pp. 499-507, XP019841523, ISSN: 1432-0614.
Erwin H. Duitman et al.; The mycosubtilin synthetase of Bacillus subtilis ATCC6633: A multifunctional hybrid between a peptide synthetase, an amnio transferase, and a fatty acid synthase; Proceedings of the National Academy of Sciences, National Academy of Sciences, US, vol. 96, No. 23, Nov. 9, 1999, pp. 13294-13299, XP002145095, ISSN: 0027-8424, DOI: 10-1073/PNAS.96.23.13294.
F. Coutte et al.; Effect of pps disruption and constitutive expression of srfA on surfactin productivity, spreading and antagonistic properties of Bacillus subtillis 168 derivatives; Journal of Applied Microbiology; vol. 109, 2010; pp. 480-491, XP2632917; ISSN: 1364-5072.
Marc Ongena et al.; Bacillus lipopeptides: versatile weapons for plant disease biocontrol; 2007 Elsevier Ltd., Trends in Microbiology, vol. 16, No. 3, pp. 115-125.
J. S. Guez et al.; Setting up and modelling of overflowing fed-batch cultures of Bacillus subtilis for the production and continuous removal of lipopeptides; Journal of Biotechnology 131 (2007) pp. 67-75; 2007 Elsevier.

(Continued)

*Primary Examiner* — Rebecca Prouty
(74) *Attorney, Agent, or Firm* — Fish & Richardson P.C.

(57) ABSTRACT

Biosurfactants produced by a strain of *Bacillus* sp and to uses thereof. A composition comprising the biosurfactants, and a method for producing the biosurfactants. A method for obtaining a biosurfactant, and a device for implementing the method. The production of biopesticides or biosurfactants for the phytosanitary industry, and in the fields of the food, cosmetics, pharmaceutical and oil industries and the environment.

5 Claims, 7 Drawing Sheets

(56) References Cited

OTHER PUBLICATIONS

D.A. Davis et al.; The production of Surfactin in batch culture by Bacillus subtilis ATCC 21332 is strongly influenced by the conditions of nitrogen metabolism; Enzyme and Microbial Technology 25 (1999) pp. 322-329; 1999 Elsevier.

M. Landy et al.; Bacillomycin: An Antibiotic from Bacillus subtilis Active against Pathogenic Fungi; Experimental Biology and Medicine; Exp Biol Med (Maywood) 1948 67:539; DOI: 10-3181/00379727-67-16367; http://ebm.sagepub.com/content/67/4/539; Apr. 17, 2014; pp. 539-541.

J.S. Guez et al.; Respiration activity monitoring system (RAMOS), an efficient tool to study the influence of the oxygen transfer rate on the synthesis of lipopeptide by Bacillus subtilis ATCC6633; Journal of Biotechnology 134 (2008) pp. 121-126; DOI: 10-1016/j.jbiotec.2008.01.003; Science Direct Elsevier 2008.

Giuseppe Bertani; Lysogeny at Mid-Twentieth Century: P1, P2, and Other Experimental Systems: Journal of Bacteriology, 2004, 186(3):595. DOI: 10-1128/JB.186.3.595-600 (2004) pp. 595-600; vol. 186, No. 3; American Society for Microbiology.

David Dubnau; Genetic Transformation in Bacillus subtilis; The Molecular Biology of the Bacilli, vol. I Bacillus subtilis. Academic Press, Inc. New York (1982); pp. 148-178.

Francoise Besson et al.; Antifungal Activity Upon *Saccharomyces cerevisiae* of Iturin A. Mycosubtilin, Bacillomycin L and of their Derivatives; Inhibition of this Antifungal Activity by Lipid Antagonists; The Journal of Antibiotics; Aug. 1979; vol. XXXII, No. 8; pp. 828-833.

Huei-Li Chen et al.; Separation of surfactin from fermentation broths by acid precipitation and two-stage dead-end ultrafiltration processes; Elsevier—Journal of Membrane Science Science Direct; DOI:10.1016/j.memsci.2007.04.031; 299 (2007) pp. 114-121.

Huei-Li Chen et al.; Flux decline and membrane cleaning in cross-flow ultrafiltration of treated fermentation broths for surfactin recovery; Elsevier, ScienceDirect; Separation and Purification Technology; DOI: 10-1016/j.seppur.2007.12.015; 62 (2008) pp. 47-55.

Joseph Sambrook et al.; Molecular Cloning, A Laboratory Manual, vol. 1, Third Edition; Cold Spring Harbor Laboratory Press, Cold Spring Harbor, N.Y., Protocol 1—sections 1.32 to 1.34, Protocol 15—Section 5.68-5.70 and Protocol 17, 18, 19—sections 1.84-1.92, 2001.

Jonathan J. Dennis et al.; Plasposons: Modular Self-Cloning Minitransposon Derivatives for Rapid Genetic Analysis of Gram-Negative Bacterial Genomes; Applied and Environmental Microbiology, 1998, vol. 64, No. 7: pp. 2710-2715. American Society for Microbiology.

Marta Herrero et al.; Transposon vectors containing non-antibiotic resistance selection markers for cloning and stable chromosomal insertion of foreign genes in gram-negative bacteria, Journal of Bacteriology; American Society for Microbiology; Nov. 1990, vol. 172, No. 11, pp. 6557-6567.

Sonenshein A, "Control of key metabolic intersections in Bacillus subtilis." Nat Rev Microbiol. Dec. 2007;5(12):917-27.

Marahiel et al., "Modular Peptide Synthetases Involved in Nonribosomal Peptide Synthesis." Chem. Rev., 1997, 97 (7), pp. 2651-2674.

Bechet et al., "Production of a novel mixture of mycosubtilins by mutants of Bacillus subtilis."Bioresour Technol. Oct. 2013;145:264-70.

* cited by examiner

SEQUENCE LISTING

```
<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /organism="Artificial Sequence"
      /note="amorce PBP-FO2"
      /mol_type="unassigned DNA"

<400> SEQUENCE: 1
aataacggac atgccgaagt g                                         21

<210> SEQ ID NO 2
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /organism="Artificial Sequence"
      /note="amorce FENF-REV2"
      /mol_type="unassigned DNA"

<400> SEQUENCE: 2
```
aataggccga ccaagacgtt c                                    21

<210> SEQ ID NO 3
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /organism="Artificial Sequence"
      /note="amorce SRF-FO"
      /mol_type="unassigned DNA"

<400> SEQUENCE: 3
acaggaatat gctcaatcga ag                                   22

<210> SEQ ID NO 4
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /organism="Artificial Sequence"
      /note="amorce SRF-REV"
      /mol_type="unassigned DNA"

<400> SEQUENCE: 4
aaattcgctt ccaggcttct g                                    21

<210> SEQ ID NO 5
<211> LENGTH: 37
<212> TYPE: DNA
<213> ORGANISM: Artificial Sequence
<220> FEATURE:
<221> NAME/KEY: source
<222> LOCATION: 1..37
<223> OTHER INFORMATION: /organism="Artificial Sequence"
      /note="amorce TETP1"
      /mol_type="unassigned DNA"

<400> SEQUENCE: 5
gttgtatcga tgatgaaata ctgaattta aacttag                    37

<210> SEQ ID NO 6
<211> LENGTH: 34
<212> TYPE: DNA
<213> ORGANISM: Artificial Sequence
<220> FEATURE:
<221> NAME/KEY: source
<222> LOCATION: 1..34
<223> OTHER INFORMATION: /organism="Artificial Sequence"
      /note="amorce TETT1"
      /mol_type="unassigned DNA"

<400> SEQUENCE: 6
tttaatggat ctagaagatt tgaattcctg ttat                      34

<210> SEQ ID NO 7
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /organism="Artificial Sequence"
      /note="amorce pC194cmfwd"
      /mol_type="unassigned DNA"

<400> SEQUENCE: 7
agaaagcaga caggtaaccc tcctaa                                              26

<210> SEQ ID NO 8
<211> LENGTH: 26
<212> TYPE: DNA
<213> ORGANISM: Artificial Sequence
<220> FEATURE:
<221> NAME/KEY: source
<222> LOCATION: 1..26
<223> OTHER INFORMATION: /organism="Artificial Sequence"
      /note="amorce pC194cmrev"
      /mol_type="unassigned DNA"

<400> SEQUENCE: 8
gcaggttagt gacattaggt aaccga                                              26

<210> SEQ ID NO 9
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /organism="Artificial Sequence"
      /note="amorce SRFAA5-FWD"
      /mol_type="unassigned DNA"

<400> SEQUENCE: 9
aaggaatctc gcaatcattt atcg                                                24

<210> SEQ ID NO 10
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /organism="Artificial Sequence"
      /note="amorce SRFAA5REV"
      /mol_type="unassigned DNA"

<400> SEQUENCE: 10
cttggtgtaa gcggaatttc tgtc                                                24

<210> SEQ ID NO 11
<211> LENGTH: 2635
<212> TYPE: DNA
<213> ORGANISM: Artificial Sequence
<220> FEATURE:
<221> NAME/KEY: source
<222> LOCATION: 1..2635
<223> OTHER INFORMATION: /organism="Artificial Sequence"
      /note="Fragment SphI-SacI de pBG106 ayant servi C la construction
      de BBG116 (opC)ron myc sous le contrC4le de PrepU-neo)"
      /mol_type="unassigned DNA"

<400> SEQUENCE: 11
gcatgcaaaa aatggtactt tcatcacttc atgttcaaaa ttacgacaaa aaacgaaacg         60
aaaactaaag aaataatact attttcaaaa aagtacaatg aaaaatttac atttttatt        120 gtactttaat aaatatacgt taatatagtg catatatgga ttatatagcc atataattta        180
tttttctgtc attatttcac tttcttaacc tcttatttta gaactgaggg aattgttgag        240
ccgaacatct tattctttac cttgcccaaa agaaagtaca gtttatcgac ctgttggttg        300
ttccagtgtt ttttgcaggt gattccagca ttcatagttg cagaagtatt atctaagtca        360
ttgttaaacc tgtatcgtct tagccagcct tattttggcg tggtaattat aggccaatct        420

```
caagactagc aggacaagct tccgcaaaca atagcttcta aagtagaaac tccatatgtc    480
gcgttgctca atcaagtaaa gttttttggc gagttgcaac gtcatctgtg tccgtccctg    540
gcagttttat ctgccgcggg cttctcaccc ttgctcttgt tttgttttcc tccacctaga    600
gctattcaac tataatcaaa cgcaatcaaa tcttgaacac cctcagagac atacaaacgc    660
atcaattaaa aaaagacgtt taatcgttag gcttccatta tttgagctgc aattatgaca    720
atgatcccat atgcaggtcg actctagagc ttgggctgca ggtcgagatc agggaatgag    780
tttataaaat aaaaaaagca cctgaaaagg tgtctttttt tgatggtttt gaacttgttc    840
tttcttatct tgatacatat agaaataacg tcatttttat tttagttgct gaaaggtgcg    900
ttgaagtgtt ggtatgtatg tgttttaaag tattgaaaac ccttaaaatt ggttgcacag    960
aaaaacccca tctgttaaag ttataagtga ctaaacaaat aactaaatag atgggggttt   1020 ctttttaatat tatgtgtcct aatagtagca tttattcaga tgaaaaatca agggttttag   1080
tggacaagac aaaaagtgga aaagtgagac catgagctta tgcttaggaa gacgagttat   1140
taatagctga ataagaacgg tgctctccaa atattcttat ttagaaaagc aaatctaaaa   1200
ttatctgaaa agggaatgag aatagtgaat ggaccaataa taatgactag agaagaaaga   1260
atgaagattg ttcatgaaat taaggaacga atattggata aatatgggga tgatgttaag   1320
gctattggtg tttatggctc tcttggtcgt cagactgatg gccctattc ggatattgag   1380 atgatgtgtg tcatgtcaac agaggaagca gagttcagcc atgaatggac aaccggtgag   1440
tggaaggtgg aagtgaattt tgatagcgaa gagattctac tagattatgc atctcaggtg   1500
gaatcagatt ggccgcttac acatggtcaa tttttctcta ttttgccgat ttatgattca   1560
ggtggatact agagaaagt gtatcaaact gctaaatcgg tagaagccca acgttccac    1620 gatgcgattt gtgcccttat cgtagaagag ctgtttgaat atgcaggcaa atggcgtaat   1680
attcgtgtgc aaggaccgac aacatttcta ccatccttga ctgtacaggt agcaatggca   1740
ggtgccatgt tgattggtct gcatcatcgc atctgttata cgacgagcgc ttcggtctta   1800
actgaagcag ttaagcaatc agatcttcct tcaggttatg accatctgtg ccagttcgta   1860
atgtctggtc aactttccga ctctgagaaa cttctggaat cgctagagaa tttctggaat   1920
gggattcagg agtggacaga acgacacgga tatatagtgg atgtgtcaaa acgcatacca   1980
ttttgaacga tgacctctaa taattgttaa tcatgttggt tacgtattta ttaacttctc   2040
ctagtattag taattatcag aattgatctg cggccgcgaa ttcaagctct agaagattgg   2100
agggagctaa tgaataatct tgccttttta tttccgggac aaggttctca gtttgttggg   2160
atgggtaaaa gttttggaa tgattttgtg ctggcgaaga gattatttga agaggcaagc   2220
gatgccatct ccatggatgt aaaaaagttg tgctttgatg gcgatatgac tgaattgaca   2280
aggacaatga atgcacagcc tgccattta acggttagtg ttatcgctta tcaagtatat   2340
atgcaggaaa taggaattaa accgcacttt tggcaggtc acagcttggg cgaatattca   2400
gcgcttgtct gtgcaggtgt cctttctttt caagaagccg ttaagcttat aaggcagcga   2460
ggaatactca tgcaaaatgc agatcctgag caactgggca cgatggccgc aatcacacag   2520
gtttatatcc aaccgctaca agacctgtgt acggaaattt cgacggaaga cttcccggta   2580
ggcgtggcgt gcatgaactc ggatcaacag catgtcatct ccgggtaccg agctc        2635
```

<210> SEQ ID NO 12
<211> LENGTH: 736
<212> TYPE: DNA

```
<213> ORGANISM: Artificial Sequence
<220> FEATURE:
<221> NAME/KEY: source
<222> LOCATION: 1..736
<223> OTHER INFORMATION: /organism="Artificial Sequence"
      /note="cassette "e"pbp"
      /mol_type="unassigned DNA"

<400> SEQUENCE: 12
aaaaaatggt actttcatca cttcatgttc aaaattacga caaaaaacga aacgaaaact    60
aaagaaataa tactattttc aaaaaagtac aatgaaaaat ttacattttt tattgtactt   120
taataaatat acgttaatat agtgcatata tggattatat agccatataa tttatttttc   180
tgtcattatt tcactttctt aacctcttat tttagaactg agggaattgt tgagccgaac   240
atcttattct ttaccttgcc caaagaaag tacagtttat cgacctgttg gttgttccag    300
tgttttttgc aggtgattcc agcattcata gttgcagaag tattatctaa gtcattgtta   360
aacctgtatc gtcttagcca gccttatttt ggcgtggtaa ttataggcca atctcaagac   420
tagcaggaca agcttccgca aacaatagct tctaaagtaa aaactccata tgtcgcgttg   480
ctcaatcaag taaagttttt tggcgagttg caacgtcatc tgtgtccgtc cctggcagtt   540
ttatctgccg cgggcttctc acccttgctc ttgttttgtt ttcctccacc tagagctatt   600
caactataat caaacgcaat caaatcttga cacccctcag agacatacaa acgcatcaat   660 taaaaaaga cgtttaatcg ttaggcttcc attatttgag ctgcaattat gacaatgatc    720
ccatatgcag gtcgac                                                   736

<210> SEQ ID NO 13
<211> LENGTH: 1339
<212> TYPE: DNA
<213> ORGANISM: Artificial Sequence
<220> FEATURE:
<221> NAME/KEY: source
<222> LOCATION: 1..1339
<223> OTHER INFORMATION: /organism="Artificial Sequence"
      /note="cassette PrepU-neo"
      /mol_type="unassigned DNA"

<400> SEQUENCE: 13
gcttgggctg caggtcgaga tcagggaatg agtttataaa ataaaaaaag cacctgaaaa    60
ggtgtctttt tttgatggtt ttgaacttgt tctttcttat cttgatacat atagaaataa   120
cgtcattttt attttagttg ctgaaaggtg cgttgaagtg ttggtatgta tgtgttttaa   180
agtattgaaa acccttaaaa ttggttgcac agaaaaaccc catctgttaa agttataagt   240
gactaaacaa ataactaaat agatgggggt ttcttttaat attatgtgtc ctaatagtag   300
catttattca gatgaaaaat caagggtttt agtggacaag acaaaagtg gaaagtgag    360 accatgagct tatgcttagg aagacgagtt attaatagct gaataagaac ggtgctctcc   420
aaatattctt atttagaaaa gcaaatctaa aattatctga aagggaatg agaatagtga    480 atggaccaat aataatgact agagaagaaa gaatgaagat tgttcatgaa attaaggaac   540
gaatattgga taaatatggg gatgatgtta aggctattgg tgtttatggc tctcttggtc   600
gtcagactga tgggccctat tcggatattg agatgatgtg tgtcatgtca acagaggaag   660
cagagttcag ccatgaatgg acaaccggtg agtggaaggt ggaagtgaat tttgatagcg   720
aagagattct actagattat gcatctcagg tggaatcaga ttggccgctt acacatggtc   780 aattttctc tattttgccg atttatgatt caggtgata cttagagaaa gtgtatcaaa    840
ctgctaaatc ggtagaagcc caaacgttcc acgatgcgat ttgtgccctt atcgtagaag   900
```

```
agctgtttga atatgcaggc aaatggcgta atattcgtgt gcaaggaccg acaacatttc      960
taccatcctt gactgtacag gtagcaatgg caggtgccat gttgattggt ctgcatcatc     1020
gcatctgtta tacgacgagc gcttcggtct taactgaagc agttaagcaa tcagatcttc     1080
cttcaggtta tgaccatctg tgccagttcg taatgtctgg tcaactttcc gactctgaga     1140
aacttctgga atcgctagag aatttctgga atgggattca ggagtggaca gaacgacacg     1200
gatatatagt ggatgtgtca aaacgcatac cattttgaac gatgacctct aataattgtt     1260
aatcatgttg gttacgtatt tattaacttc tcctagtatt agtaattatc agaattgatc     1320
tgcggccgcg aattcaagc                                                  1339

<210> SEQ ID NO 14
<211> LENGTH: 536
<212> TYPE: DNA
<213> ORGANISM: Artificial Sequence
<220> FEATURE:
<221> NAME/KEY: source
<222> LOCATION: 1..536
<223> OTHER INFORMATION: /organism="Artificial Sequence"
      /note="cassette "e"fenF"
      /mol_type="unassigned DNA"

<400> SEQUENCE: 14
agattggagg gagctaatga ataatcttgc ctttttattt ccgggacaag gttctcagtt       60
tgttgggatg ggtaaaagtt tttggaatga ttttgtgctg gcgaagagat tatttgaaga     120
ggcaagcgat gccatctcca tggatgtaaa aaagttgtgc tttgatggcg atatgactga     180
attgacaagg acaatgaatg cacagcctgc cattttaacg gttagtgtta tcgcttatca     240
agtatatatg caggaaatag gaattaaacc gcacttttg gcaggtcaca gcttgggcga     300
atattcagcg cttgtctgtg caggtgtcct ttcttttcaa gaagccgtta agcttataag     360
gcagcgagga atactcatgc aaaatgcaga tcctgagcaa ctgggcacga tggccgcaat     420
cacacaggtt tatatccaac cgctacaaga cctgtgtacg gaaatttcga cggaagactt     480
cccggtaggc gtggcgtgca tgaactcgga tcaacagcat gtcatctccg ggtacc        536
```

BACILLUS SP. BIOSURFACTANTS, COMPOSITION INCLUDING SAME, METHOD FOR OBTAINING SAME, AND USE THEREOF

BACKGROUND

Technical Field

The present invention relates to a strain of *Bacillus* sp.

The present invention also relates to biosurfactants produced by a strain of *Bacillus* sp and to uses thereof. It also relates to a composition comprising these biosurfactants, as well as a method for producing these biosurfactants.

The present invention also relates to a method for obtaining a biosurfactant, as well as to a device for implementing this method.

The present invention finds in particular applications in the production of biopesticides or biosurfactants for the plant health industry, and also in the fields of the food, cosmetics, chemical, pharmaceutical and oil industries and the environment.

In the following description, the references between ([ ]) refer to the list of references presented at the end of the examples.

Prior Art

The conventional agricultural production system uses plant-health products of the pesticide type in order to ensure sufficient production in terms of quantity and quality, in accordance with the expectations of the markets and at a cost acceptable to the consumer. Though the use of these products affords benefits for the agricultural systems, it may nevertheless give rise to negative effects for human health and for the environment. Degradation of the quality of subterranean water and surface water and reduction in biodiversity in the agricultural environment are the consequences most frequently cited.

Biosurfactants, in particular of bacterial origin, are known to have numerous interesting properties, in particular surfactant, antiviral, antibacterial and antifungal properties able to be exploited in the plant-health field. These biosurfactants can be used alone or in a mixture of several biosurfactants. Synergetic effects have been shown when the biosurfactants are used in the form of mixtures (Ongena and Jacques, 2008 *Bacillus* lipopeptides: versatile weapons for plant disease biocontrol. Trends Microbiol. 16, 115-125 [1]; CZ20011620 [2]; DE 102005050123 [3]).

These biosurfactants have better biodegradability, lower toxicity and greater physicochemical resistance compared with a pesticide of chemical origin. Moreover, the cosmetic market has a particular stake in molecules of biological origin, which combine antimicrobial activities and physicochemical properties such as emulsifiers.

Biosurfactants are also used in the assisted recovery of oil contained in deposits, where the injection of biosurfactants reduces the viscosity of the oil and substantially improves the proportion of oil recovered. They are also used for combatting the pollution of water by hydrocarbons and are much more effective than chemical surfactants. Furthermore, these biosurfactants are not toxic for the ecosystem of the water treated.

The demand for biosurfactants has therefore increased over the past few years, in particular in the food, cosmetics, chemical, pharmaceutical and oil industries and the environment. Many production methods have been studied and used and have been the subject of publications or patent application filings (FR 2578552 [4]).

However, the biosurfactants currently available are not very effective and have limited biological and/or chemical properties.

There therefore exists a real need to provide alternative biosurfactants, preferably having improved properties compared with the biosurfactants of the prior art.

Moreover, there currently exists a real need to have available effective means for obtaining biosurfactants.

The methods for producing biosurfactants produced by *Bacillus* sp. have been particularly studied. However, these methods lead to the formation of foam caused by the addition of oxygen, in the form of bubbles. A first approach is to use aerated reactors that are mechanically agitated and to continuously extract the foam caused by the biosurfactant and containing the latter. This method is laborious and not very open to use, in particular on a large scale (Guez et al., 2007. Setting up and modelling of overflowing fed-batch cultures of *Bacillus subtilis* for the production and continuous removal of lipoeptides. J Biotechnol, 131, 67-75 ([5]).

In order to avoid this problem of foam, attempts have been made to work under anaerobic conditions and to use nitrate as the final electron acceptor (Davis, Lynch and Varley. 1999. The production of surfactin in batch culture by *Bacillus subtilis* ATCC 21332 is strongly influenced by the conditions of nitrogen metabolism. Enzyme Microb. Technol. 25, 322-329. [6]; WO 0226961 [7]; EP 1320595 [8]). Productions of biosurfactants depend greatly on the ability of the strains to adapt or not to these anaerobic conditions. No effective solution making it possible to produce biosurfactants in industrial quantities has been developed up to the present time. Moreover, the use of pesticides of chemical origin being more and more contested, it is necessary to research and use molecules of biological origin in order to replace pesticides of chemical origin and to develop methods for producing these molecules of biologic origin on an industrial scale.

There therefore exist real requirements to develop a method and device overcoming these defects, drawbacks and obstacles of the prior art, including a method for continuously producing biosurfactants in large quantities with low production costs.

SUMMARY

The present invention precisely meets the aforementioned requirements, by providing a *Bacillus subtilis* strain, mycosubtilins, a composition comprising these mycosubtilins, and a method for obtaining these mycosubtilins.

The present invention also provides a method and device for producing a biosurfactant on an industrial scale, in particular by eliminating or limiting the formation of foam.

The subject matter of the present invention is thus a method for obtaining a biosurfactant, comprising a step (a) of culture of a microorganism capable of producing a biosurfactant in a culture medium comprising an organic substrate, the culture of the microorganism being performed on the surface of an air/liquid membrane contactor.

The inventors are in fact the very first to have implemented this method and have discovered, surprisingly, that the immobilisation of the cells on the air/liquid membrane contactor is particularly favourable to the production of biosurfactants continuously, while avoiding the formation of foam. Furthermore, the method according to the invention increases the biosurfactant production yield. In addition, the use of an air/liquid membrane contactor in the method according to the present invention makes it possible to produce a biosurfactant continuously.

Hereinafter, "biosurfactant" means a surface-active molecule that is amphiphilic and is produced from a microorganism. It may for example be a compound chosen from the group comprising a lipopeptide, a phospholipid, a glycolipid, a lipoprotein, or a fatty acid ester. For example, the lipopeptide is chosen from the group comprising an iturin, a surfactin, a mycosubtilin, a syringomycin, a fengycin (or plipastatin), a lichenysin, a bacillomycin, a kurstakin, a tolaasin, an arthrofactin, a serrawettin, a putisolvin and a massetolide. The phospholipid may for example be chosen from the group comprising a phosphatidylcholine. The ester may for example be chosen from the group comprising a sorbitan or rhamnose ester, a monomyristin, a monolinolein and a monolinolenin. The glycolipid may for example be a rhamnolipid.

"Culture of a microorganism" means all the techniques used for growing a microorganism and/or making it produce one or more molecules.

"Microorganism capable of producing a biosurfactant" means any unicellular or pluricellular microscopic organism devoid of tissue differentiation, and having the ability to synthesise a biosurfactant. It may for example be a bacterium, a yeast, a mould or an alga.

For example, the bacterium may belong to the genus chosen from the group comprising *Bacillus, Pseudomonas, Rhodococcus, Acinetobacter, Serratia, Burkholderia, Mycobacterium, Nocardia, Flavobacterium, Corynebacterium, Clostridium, Thiobacillus, Arthrobacter, Alcanivorax* and *Paenibacillus*. For example, the yeast may belong to a genus chosen from the group comprising *Candida, Pseudozyma, Ustilago, Schizonella, Kurtzmanomyces, Torulopsis, Rhodotorula* and *Wickerhamiella*. Preferably, the microorganism capable of producing a biosurfactant belongs to the genus *Bacillus*.

When the microorganism capable of producing a biosurfactant belongs to the genus *Bacillus*, it may for example be chosen from the group comprising *Bacillus subtilis, Bacillus thuringiensis, Bacillus licheniformis, Bacillus amyloliquefaciens, Bacillus cereus, Bacillus pumilus* and *Bacillus mojavensis*. It may for example be a case of strains chosen from the group comprising *Bacillus subtilis*, such as the one filed on 10 Mar. 2011 under the number CNCM 1-4451 in the National Collection of Microorganism Cultures (CNCM) of the Institut Pasteur (Paris, France). Also called *Bacillus subtilis* BBG125, as well as *Bacillus subtilis* ATCC 21332, *Bacillus subtilis* BBG21, *Bacillus subtilis* ATCC 6633, *Bacillus subtilis* BBG100, *Bacillus subtilis* ATCC 9943, *Bacillus subtilis* S499, *Bacillus subtilis* BBG116, *Bacillus subtilis* BBG131, *Bacillus licheniformis* BAS50, a strain derived from *Bacillus licheniformis* ATCC 14580 and *Bacillus thuringiensis* BBG300.

Preferably, for producing micosubtilin, the microorganism capable of producing a biosurfactant is chosen from the group comprising *Bacillus subtilis* BBG125, *Bacillus subtilis* BBG100 and *Bacillus subtilis* BBG1116, preferably from the group comprising *Bacillus subtilis* BBG125 and *Bacillus subtilis* BBG100.

Preferably, for producing surfactin, the microorganism capable of producing a biosurfactant is *Bacillus subtilis* BBG131.

Preferably, for producing fengycin, the microorganism capable of producing a biosurfactant is chosen from the group comprising *Bacillus subtilis* ATCC 21332 and *Bacillus subtilis* BBG21.

Preferably again, according to the invention, the microorganism capable of producing a biosurfactant is *Bacillus subtilis* BBG125.

When the microorganism capable of producing a biosurfactant belongs to the genus *Pseudomonas*, it may for example be chosen from the group comprising *Pseudomonas aeruginosa, Pseudomonas cichorii, Pseudomonas putida, Pseudomonas fluorescens, Pseudomonas stutzeri, Pseudomonas syringae* and *Pseudomonas tolaasii*.

Hereinafter, "organic substrate" means any substance or mixture of substances making it possible to grow the microorganism and/or to make it produce one or more molecules. For example, the organic substrate may be chosen from the group comprising starch, glucose, glutamate, saccharose, xylose, glycerol, the organic acids, amino acids and a mixture of these organic substrates. For example, the organic substrate may be the Landy medium with the following composition: glucose, 20 g/liter; glutamic acid, 5 g/liter; yeast extract, 1 g/liter, $K_2HPO_4$, 1 g/liter; $MgSO_4$, 0.5 g/liter, KCl, 0.5 g/liter, $CuSO_4$, 1.6 mg/liter; $Fe_2(SO_4)_3$, 1.2 mg/liter, $MnSO_4$, 0.4 mg/liter (Landy et al. 1948. Bacillomycin; an antibiotic from *Bacillus subtilis* active against pathogenic fungi. Proc. Soc. Exp. Biol. Med. 67, 539-541) [9]. The organic substrate may also for example be a modified Landy medium, for example a Landy medium supplemented with ammonium sulfate at 2.3 g/liter and/or the glutamic acid concentration is 2 g/liter (Guez et al, 2008. Respiration activity monitoring system (RAMOS), an efficient tool to study the influence of the oxygen transfer rate on the synthesis of lipopeptide by *Bacillus subtilis*. J. Biotechnol. 134, 121-126 [10]).

Hereinafter, "air/liquid contactor" means a device for oxygenating a liquid medium using a gas containing oxygen. An air/liquid contactor comprises in particular an air/liquid membrane contactor. It may for example be a case of a reactor comprising an air/liquid membrane contactor. By way of examples of air/liquid contactor, the following contactors can be mentioned: "Hollow fibre cartridges" from GE Healthcare in accordance with the models defined by references commencing with CFP, and "Hollow fibre modules" from Spectrum Labs in accordance with the models defined by the references commencing with KM.

An air/liquid membrane contactor also separates the liquid phase from the gaseous phase: the gaseous phase circulates on one side of the membrane and the liquid phase flows on the other side (Remize and Cabassud 2003, A novel bubble-free oxidation reactor: the G/L membrane contactor. Recent progress in method engineering. Integration of membranes in the methods 2. Lavoisier Tec and Doc. [11]), without these two phases mixing.

"Air/liquid membrane contactor" means a porous membrane allowing the diffusion of oxygen in a culture medium.

For example, the air/liquid membrane contactor may be a membrane made from hollow fibres or flat membranes.

The air/liquid membrane contactor may for example have pores with a size of between 0.01 and 2 µm, for example between 0.01 and 1 µm, for example between 0.1 and 0.65 µm.

The air/liquid membrane contactor may for example have a surface area of between 0.1 and 20 $m^{-2}$. The surface area of the air/liquid membrane contactor is preferably greater than 1 $m^{-2}$.

The air/liquid membrane contactor may for example be a hydrophobic membrane, guaranteeing better separation of these two phases. For example, the air/liquid membrane contactor may be produced from a material chosen from the group of polymers comprising polyethersulfone, polypropylene, polysulfone, regenerated cellulose and cellulose esters.

The air/liquid membrane contactor may for example be flat, cylindrical, cylindroconical or any geometric shape optimising the microorganism culture and exchanges with oxygen.

By way of example of air/liquid membrane contactors, the following membranes can in particular be mentioned:
- (CFP-6-D-45) from GE-Healthcare Europe GmbH (Munich, Germany),
- hollow-fibre filtration modules (Hollow fibre cartridges) from GE Healthcare in accordance with the models defined by the references commencing with CFP,
- hollow fibre filtration modules (Hollow fibre modules) from Spectrum Labs in accordance with the models defined by the references commencing with KM.

According to the invention, the microorganisms capable of producing a biosurfactant may be immobilised actively either completely or partially on the surface of the air/liquid membrane contactor. In other words, a major part of the microorganisms present in the air/liquid contactor are immobilised on the surface of the membrane of this contactor, the other part being in suspension in the culture medium after release thereof.

Thus the method according to the invention may comprise a step (a) of culturing a microorganism capable of producing a biosurfactant in a culture medium comprising an organic substrate, the microorganism being cultured on the surface of an air/liquid membrane contactor. In other words, the method of the present invention advantageously makes it possible to dispense with a culture dish or a fermenter. The method according to the invention advantageously makes it possible to produce mycosubtilins continuously and in highly satisfactory quantities. Advantageously, the method of the present invention is implemented continuously. A culture dish or fermenter may be added optionally but is not essential. The addition of a culture dish or a fermenter is rather inadvisable since it would reduce the production yields. Thus, advantageously, the method of the present invention is implemented in a device not comprising a culture dish or a fermenter. In other words, according to the method of the invention, the culture of the microorganism capable of producing a biosurfactant can be carried out on the surface of the air/liquid membrane contactor only.

The oxygen necessary for the microorganisms capable of producing a biosurfactant is transferred by diffusion through the pores of the air/liquid membrane contactor where said microorganisms are immobilised. In other words, according to the invention, the oxygenation of the microorganism medium is not done by a bubbling system situated in a reactor nor by an oxygenation system situated outside the microorganism culture reactor.

The oxygen flow of the air/liquid membrane contactor can be adjusted to any flow rate making it possible to oxygenate the microorganisms capable of producing a biosurfactant. A person skilled in the art is able to determine the oxygen flow rates of the air/liquid membrane contactor according to the required addition of oxygen. The inventors have found that an aeration flow of between 0.2 and 2 volumes of air per volume of liquid per minute (vvm) is particularly effective for oxygenating the culture medium and the microorganisms. The air flow of the air/liquid contactor can therefore for example be between 1.5 and 2 vvm. Preferably, the aeration flow of the air/liquid contactor is 0.25 vvm for producing mycosubtilin. Preferably, the aeration flow rate of the air/liquid contactor is 1 vvm for producing surfactin. Preferably, the aeration flow rate of the air/liquid contactor is 0.5 vvm for producing fengycin.

According to the method of the invention, the culture step (a) can be performed on the surface of a plurality of air/liquid membrane contactors. For example, the culture step (a) can be performed on the surface of two air/liquid membrane contactors, for example 3, 4, 5, 6, 7, 8, 9, 10 air/liquid membranes, or even more. A person skilled in the art is able to determine the number of air/liquid membrane contactors according to the quantity of biosurfactant to be produced.

One of the objectives of the present invention is to increase the quantity of microorganisms immobilised on the surface of the air/liquid membrane contactor. This can be done by increasing the surface area of the air/liquid membrane contactor and/or the number of air/liquid membrane contactors.

When the culture step (a) is performed on the surface of a plurality of air/liquid membrane contactors, the air/liquid membrane contactors may for example be disposed in series or in parallel. Preferably, when the culture step (a) is performed on the surface of a plurality of air/liquid membrane contactors, the air/liquid membrane contactors are disposed in parallel.

The method of the present invention may further comprise a step of separating the biosurfactant from the culture medium containing it. This separation step may be performed by any means known to persons skilled in the art making it possible to separate a substance contained in a liquid medium thereof.

For example, the step of separating the biosurfactant from the culture medium containing it may comprise one or more steps, chosen from the group comprising microfiltration, ultrafiltration, nanofiltration and centrifugation.

For example, the step of separating the biosurfactant from the culture medium containing it comprises the following steps:
- (b) microfiltration of the culture medium obtained at step (a), for separating the microorganism from the culture medium, and/or
- (c) ultrafiltration of the culture medium obtained at step (a) or (b), for separating the biosurfactant from the culture medium obtained at step (a) or (b).

Preferably, the separation step comprises each of steps (b) and (c).

The steps of microfiltration (b) and ultrafiltration (c) make it possible to continuously extract the biosurfactant from the culture medium obtained at step (a) and/or (b).

Combining the air/liquid membrane contactor with the microfiltration (b) and ultrafiltration (c) steps thus makes it possible to continuously produce and extract a biosurfactant from a microorganism capable of producing it.

The microfiltration step (b) can be performed with any microfiltration means making it possible to separate the microorganism from the culture medium containing it. For example, the microfiltration means may be a microfiltration membrane. For example, the microfiltration means may be a microfiltration membrane. For example, the microfiltration means may be an organic or mineral microfiltration membrane, for example a hollow-fibre membrane.

The microfiltration step (b) may for example be performed with a membrane made from hollow fibres having pore sizes from 0.1 to 0.45 micrometers ($\mu m$). Preferably, the hollow-fibre membrane used at step (b) has a pore size of 0.2 $\mu m$.

By way of example of membranes that can be used for performing the microfiltration step (b), the following membranes can be cited:

hollow polysulfone or polyethersulfone fibres with a pore size of 0.2 µm, reference CFP-2-E-4X2MA (GE-Healthcare Europe GmbH, Munich, Germany), hollow polysulfone or polyethersulfone fibres with a pore size of 0.45 µm, reference CFP-4-E-4X2MA or a pore size of 0.56 µm reference CFP-2-E-6X2MA (GE-Healthcare Europe GmbH, Munich, Germany), a hollow-fibre microfiltration or ultrafiltration module (hollow fibre cartridges) from GE-Healthcare according to the models defined by references commencing with CFP, a hollow-fibre filtration module (Hollow fibre modules) from Spectrum Labs (Rancho Dominguez, Calif., USA) in accordance with the models defined by references commencing with KM, Sartocon microfiltration cassettes from Sartorius Stedim (Aubagne, France) in accordance with the models defined by references commencing with SPC20.

The ultrafiltration step (c) can be performed with any filtration means making it possible to separate the biosurfactant from the culture medium containing it, and to concentrate the biosurfactant. For example, the ultrafiltration means may be an ultrafiltration membrane, for example an ultrafiltration membrane made from regenerated cellulose.

The ultrafiltration step (c) may for example be performed with a membrane having a cutoff threshold of between 5 and 50 kilodaltons (kDa), for example between 5 kDa and 30 kDa, for example between 5 and 20 kDa. The membrane used at step (c) preferably has a cutoff threshold of 10 kDa.

By way of example of membranes that can be used for performing the ultrafiltration step (c), the following membranes can be cited:

ultrafiltration membrane with cutoff threshold of 10 kDa made from regenerated cellulose, reference 3051443901E-SW (Sartorius, Gottingen, Germany), ultrafiltration membrane with a cutoff threshold of 10 kDa made from regenerated cellulose, reference P2C010C01 (Millipore Headquarters, 290 Concord Road, Billerica, Mass., USA).

The membranes used at step (a), (b) and (c) are preferably sterilisable at 121° C. for 20 minutes.

The method according to the present invention is differentiated from the known methods for the biological degradation of organic materials by microorganisms that excrete biosurfactants in that it is possible to recycle or not all the microorganisms after having removed from them the residues of organic matter from the culture medium and biosurfactants produced. This makes it possible to obtain a high degree of concentration of the microorganisms in the bioreactor.

It is also differentiated from the known methods for the biological degradation of organic materials by microorganisms that excrete biosurfactants in that approximately 95% of the biosurfactants produced remain in the culture medium without the least formation of foam. Approximately 5% of the biosurfactants are adsorbed on the air/liquid interface of the membrane contactor, but may be desorbed for example by washing the membrane.

The air/liquid membrane contactor can be washed by any means known to persons skilled in the art in order to recover the biosurfactants produced and adsorbed at the air/liquid interface of the membrane contactor. For example, the washing of the air/liquid membrane contactor may be performed with one or more washing solutions chosen from the group comprising distilled water, an NaOH solution, an NaOCl solution, a sodium or potassium hydrogen carbonate solution, or a sodium or potassium carbonate solution. The washing solution may be brought to any pH making it possible to increase the quantity of biosurfactants recovered. For example, the washing solution is brought to a pH=10.

The washing solution may be brought to any temperature making it possible to increase the quantity of biosurfactants recovered. For example, the washing solution is brought to a temperature of between 20° and 50° C.

According to the present invention, the temperature of the culture medium may be adjusted by any heating means known to persons skilled in the art. For example, the heating means may be a heat exchanger. For example, the heat exchanger may be chosen from the group comprising a U-tube heat exchanger, a heat exchanger with a horizontal tubular cluster, a heat exchanger with a vertical tubular cluster, a spiral heat exchanger, a plate heat exchanger, a Bouhy column, or a block heat exchanger. The heating means is preferably a tubular heat exchanger.

Thus the method according to the invention can be implemented at any temperature making it possible to produce a biosurfactant from a microorganism capable of producing it. For example, the method may be implemented at a temperature between 0° C. and 70° C., advantageously between 20° C. and 37° C. Preferably, the method may be implemented at a temperature of 22° C. for producing mycosubtilin. The method may preferably be implemented at a temperature of 30° C. for producing fengycin. Preferably, the method may be implemented at a temperature of 37° C. for producing surfactin.

Moreover, the method according to the present invention may be implemented at any pH making it possible to produce a biosurfactant from a microorganism capable of producing it. The pH may be regulated by means of the controlled addition of basic solution or acid solution to the culture medium.

The basic solution may for example be chosen from the group comprising soda, potash and ammonia.

The acid solution may for example be chosen from the group comprising phosphoric acid, sulphuric acid and nitric acid.

The pH may for example be regulated to any value enabling microorganisms capable of producing a biosurfactant to survive. It may for example be regulated to a value between pH 6 and pH 8, preferably to a value of pH 7. A person skilled in the art is able to determine the quantities of basic solution and acid solution for regulating the pH to a required value.

The method according to the present invention may advantageously be implemented continuously, that is to say the supply of the air/liquid membrane contactor and the extraction of the biosurfactants produced by the microorganisms can be carried out without interruption. The method of the present invention may be performed at any hourly rate making it possible to extract a biosurfactant from a microorganism capable of producing it. The rate at which the method can be implemented, that is to say the flow rate of culture medium added to the air/liquid membrane contactor, can easily be adapted by a person skilled in the art. The inventors have found that conducting the continuous method at a dilution rate of between 0.05 $h^{-1}$ and 0.5 $h^{-1}$ is particularly effective for producing biosurfactants from microorganisms. The dilution rate is defined as the supply or extraction rate divided by the culture volume. The method according to the invention can therefore, for example, be performed at a circulating hourly rate corresponding to a degree of dilution of between 0.05 $h^{-1}$ and 0.5 $h^{-1}$, advantageously at an hourly rate of 0.1 $h^{-1}$.

Another subject matter of the present invention is a device for implementing the method described herein, said device comprising an air/liquid membrane contactor. For example, the device according to the invention comprises at least one air/liquid contactor comprising an air/liquid membrane contactor.

The air/liquid membrane contactor and the air/liquid contactor may be those defined above.

The number of air/liquid membrane contactors and air/liquid contactors may be as defined above.

The device according to the invention does not comprise any aeration means other than the membrane or the plurality of air/liquid membrane contactors. In other words, the device according to the invention does not comprise a bubbling system situated in a reactor. It also does not comprise an oxygenation system situated outside the microorganism culture reactor. The device according to the present invention may further comprise a microfiltration means and/or an ultrafiltration means. The device according to the invention preferably comprises a microfiltration means and an ultrafiltration means. The microfiltration means and the ultrafiltration means may for example be those described above.

Advantageously, the device according to the invention comprises the means necessary for continuously implementing the method according to the invention. In other words, the device advantageously comprises a means for introducing a culture medium and a means for taking off the biosurfactant produced by the microorganism. Any introduction means and take-off means known to persons skilled in the art for obtaining a device for continuously implementing the method according to the invention may be used.

The device according to the invention may further comprise an evaporation means. Hereinafter, "evaporation means" means any means for concentrating a biosurfactant in a medium containing it. It may for example be an evaporation means chosen from the group comprising a vacuum evaporator of the Rotavapor VV000 type (Heidolph Instruments GmbH & Co, Schwabach, Germany) and a climbing-film evaporator. The device according to the present invention may further comprise a heating means for regulating the temperature of the culture medium. The heating means may for example be the one described above. The heating system may be connected to the air/liquid contactor via a system of pipes.

"System of pipes" means any means in which a fluid or gas may circulate. For example, the fluid may be a liquid or a gel. The system of pipes makes it possible in particular to connect together various elements of the device according to the invention. For example, the system of pipes may be any type of flexible or rigid pipework of the silicone type. (Cole Parmer, Vernon Hills, Ill., USA) or made from 316S stainless steel (Swagelok Company, Solon, Ohio, USA).

The circulation of the fluid or gas in the system of pipes may be regulated by one or more pumps and/or one or more valves.

The device according to the present invention may further comprise at least one pump.

"Pump" means, within the meaning of the present invention, means for imposing a flow rate on a liquid, for example on a culture medium in the device of the present invention. It may for example be a peristaltic pump, a lobe pump, or a membrane pump. Mention can be made for example of the Masterflex L/S peristaltic pumps compact drive model (Cole Parmer Vernon Hills, Ill., USA), Millipore Corporation (Millipore, Bedford, Mass., USA), Sartojet pump (Sartorius, Sartorius Stedim France SAS, Aubagne) and Watson-Marlow 323 (Watson Marlow, Falmouth, Cornwall, United Kingdom). Moreover, the pump may be controlled manually or automatically.

The device according to the present invention may further comprise at least one valve.

Hereinafter, "valve" means means for stopping or modifying the flow of a liquid, for example of the culture medium in the device of the present invention. It may for example be a regulation valve, a "two-state" valve, or a solenoid valve. Mention can be made for example of regulation valves made from polyvinylidene fluoride (PVDF), polypropylene (PP), perfluoroalkoxy (PFA) or stainless steel. Moreover, the valve may be controlled manually or automatically.

The inventors describe hereinafter the use of the device according to the invention for implementing the method of the invention.

Another subject matter of the present invention is a *Bacillus subtilis* strain obtained from the strain *Bacillus subtilis* ATTC 6633 in which the operon srfA coding for the synthetase surfactin has been interrupted and where the promoter of the operon myc coding for the micosubtilin synthetase has been replaced by a constitutive strong promoter $P_{repU}$.

Preferably, this *Bacillus subtilis* strain is the *Bacillus subtilis* strain filed on 10 Mar. 2011 under the number CNCM 1-4451 at the National Collection of Microorganism Cultures (CNCM) of the Institut Pasteur (Paris, France). This strain is also called *Bacillus subtilis* BBG125.

Another subject matter of the present invention is a method for producing mycosubtilins comprising a step of culturing a strain of *Bacillus subtilis* according to the invention and a step of recovering the mycosubtilins obtained.

The *Bacillus subtilis* BBG125 strain may for example be used in any method for producing biosurfactants, in particular in a method for producing C18 and C17 Gln3 mycosubtilins described above. For example, the method for producing biosurfactants may comprise a step of culturing the *Bacillus subtilis* BBG125 strain and a step of recovering the biosurfactants obtained. For example, the method for producing biosurfactants may the one of the present invention described above.

The *Bacillus subtilis* BBG125 strain developed by the inventors is particularly surprising. This strain makes it possible to produce mycosubtilins without producing surfactin. Furthermore, it makes it possible to produce mycosubtilins that have never been described.

Thus the present invention also relates to the following mycosubtilins:

C18 mycosubtilin: a mycosubtilin the fatty acid chain of which comprises 18 carbon atoms, and represented by the following formula (I):

$$CH_3-(CH_2)_{14}-\underset{\underset{NH-Asn-Ser-Pro-Gln}{|}}{CH}-CH_2-CO\text{-Asn-Tyr-Asn} \quad (I)$$

C17 mycosubtilin Gln3: a mycosubtilin the fatty acid chain of which comprises 17 carbon atoms and having a glutamine in the place of asparagine in position 3 in its peptide cycle and represented by the following formula (II):

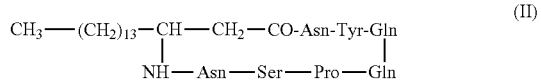

(II)

The C18 and C17 Gln3 mycosubtilins described above can be used as an antifungal agent. They moreover have antifungal effects equivalent to or even greater than the mycosubtilins currently used as an antifungal agent.

Hereinafter, "antifungal agents" means substances having the ability to treat and/or prevent infections by fungi and/or yeasts.

The inventors have also produced a composition comprising a mixture of mycosubtilins.

Thus another subject matter of the present invention is a composition comprising at least one C18 mycosubtilin and/or at least one C17 Gln3 mycosubtilin.

For example, this composition may further comprise one or more other mycosubtilins chosen from the group comprising an iso-C16 mycosubtilin, an n-C16 mycosubtilin, an anteiso-C17 mycosubtilin and an iso-C17 mycosubtilin.

When a C18 mycosubtilin is present in the composition, it may be present at a concentration of between 1% and 5% by weight of the composition.

When a C17 mycosubtilin Gln3 is present in the composition, it may be present at a concentration of between 1% and 20% by weight of the composition.

When an iso-C16 mycosubtilin is present in the composition, it may be present at a concentration of between 1% and 60% by weight of the composition.

When an n-C16 mycosubtilin is present in the composition, it may be present at a concentration of between 1% and 10% by weight of the composition.

When an anteiso-C17 mycosubtilin is present in the composition, it may be present at a concentration of between 20% and 95% by weight of the composition.

When an iso-C17 mycosubtilin is present in the composition, it may be present at a concentration of between 5% and 30% by weight of the composition.

For example, the composition according to the invention may comprise, as a percentage with respect to the weight of the composition: between 1% and 60% of iso-C16 mycosubtilin, between 1% and 20% of C17 mycosubtilin Gln3, between 1% and 10% of n-C16 mycosubtilin, between 20% and 95% of anteiso-C17 mycosubtilin, between 5% and 30% of iso-C17 mycosubtilin and between 1% and 5% of C18 mycosubtilin.

This composition preferably comprises, as a percentage with respect to the weight of the composition: 26% of iso-C16 mycosubtilin, 1% of C17 mycosubtilin Gln3, 2% n-C16 mycosubtilin, 44% anteiso-C17 mycosubtilin, 23% iso-C17 mycosubtilin and 1% C18 mycosubtilin.

This composition may for example be used as an antifungal composition. In other words, it may be a composition for use as an antifungal agent.

The composition comprising a mixture of mycosubtilins according to the present invention has an antifungal capability ranging from a minimum inhibiting concentration of 4 to 32 μm.

The mycosubtilins and the composition comprising a mixture of mycosubtilins according to the present invention can be mixed in a solution chosen from the group comprising water, ethanol, methanol, dimethylsulfoxyde (DMSO), sodium carbonate, Tris-HCl and a mixture of these solutions.

The mixture of these solutions may be a binary or ternary mixture. When the mixture of solutions is binary, the water/ethanol, water/methanol, water/DMSO, water/sodium carbonate, water/Tris-HCl, ethanol/methanol, ethanol/DMSO, ethanol/sodium carbonate, ethanol/Tris-HCl, methanol/DMSO, methanol/sodium carbonate or methanol/Tris-HCl ratio may for example be between 4/1 and 1/4, for example between 3/1 and 1/3, for example between 2/1 and 1/2, for example a ratio of 1/1, 2/1, 3/1 or 4/1. When the mixture of solutions is ternary, the water/ethanol/methanol, water/ethanol/DMSO, water/ethanol/sodium carbonate, water/ethanol Tris-HCl, water/methanol/DMSO, water/methanol/sodium carbonate, water/methanol/Tris-HCl, ethanol/methanol/DMSO, ethanol/methanol/sodium carbonate, ethanol/methanol/Tris-HCl or DMSO/sodium carbonate/Tris-HCl ratio may for example be 1/1/1, 2/1/1, 1/2/1, 1/1/2, 3/1/1, 1/3/1, 1/1/3, 3/2/1, 3/1/2, 2/3/1, 2/1/3, 1/2/3 or 1/3/2.

The mycosubtilins and the composition comprising a mixture of mycosubtilins according to the present invention may for example be used as an antifungal agent.

The present invention therefore also relates to a mycosubtilin according to the invention or a composition according to the invention for use as an antifungal agent.

The inventors therefore provide a method for the continuous production of biosurfactants making it possible to avoid the formation of foam and to increase the production yields. They have also provided a device for implementing this method as well as a strain of *Bacillus subtilis* remarkable in that it is capable of producing, in this method, mycosubtilins that have never been described and which have antifungal effects that are equivalent or even superior to the mycosubtilins currently used as an antifungal agent. The inventors have also provided an antifungal composition having antifungal effects superior to the effects of the mycosubtilins currently used.

Other advantages may also appear to a person skilled in the art from a reading of the following examples, illustrated by the accompanying figures given by way of illustration.

DETAILED DESCRIPTION

Figure 1:
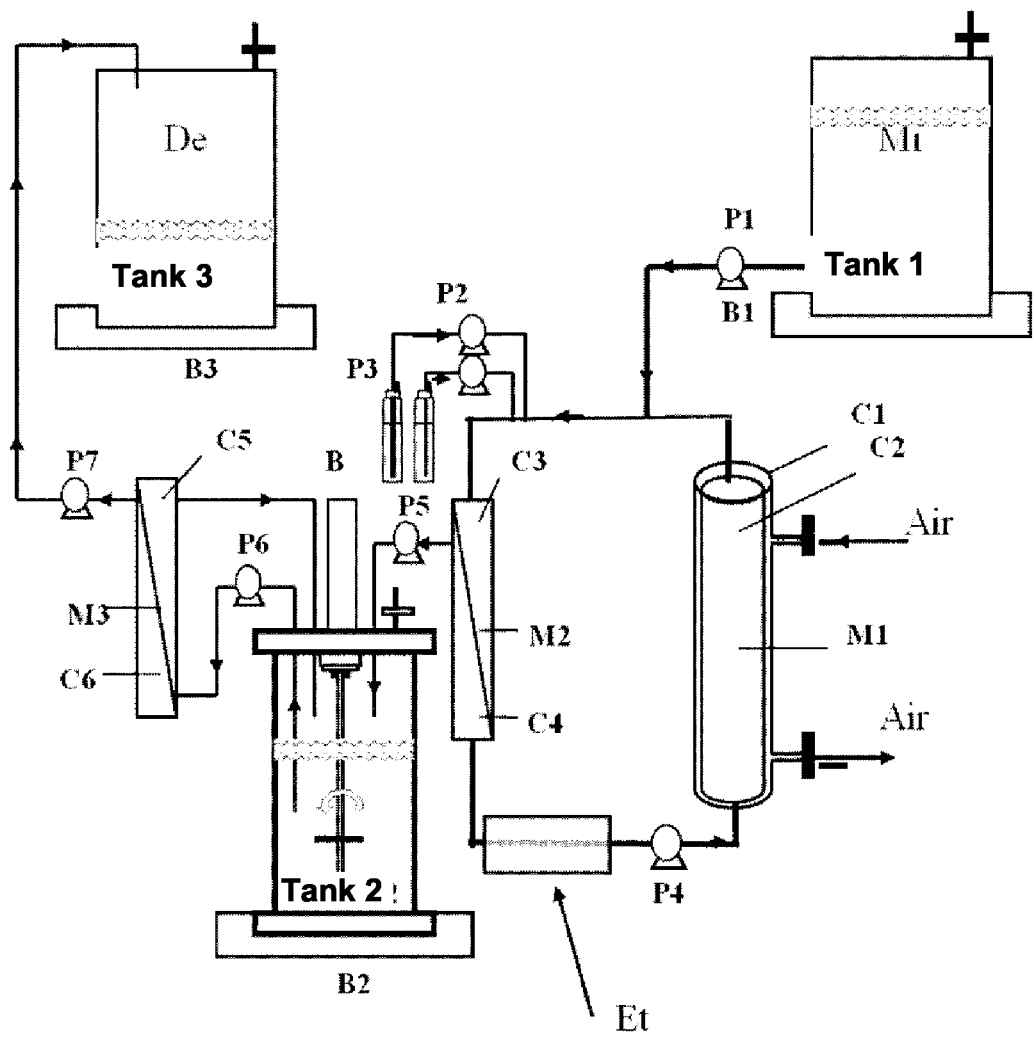
FIG. 1 is a diagram showing a device for the continuous production, without the formation of foam, and the extraction of the lipopeptides produced by a microorganism. In this figure, M1 represents an air/liquid membrane contactor made from hollow fibres having the compartments C1 and C2 representing respectively an external compartment, in which air circulates, and an internal compartment in which a culture medium circulates. M2 represents the microfiltration member of a microfiltration means having the compartments C3 and C4. M3 represents the ultrafiltration membrane of an ultrafiltration means having the compartments C5 and C6. B1, B2 and B3 each represent scales. B represents a motor for driving a stirring means in the dish 2. P1, P2, P3, P4, P5, P6 and P7 represent volumetric pumps. "Mi" means "culture medium". "De" signifies "waste" and "Et" signifies "heat exchanger".
Figure 2:
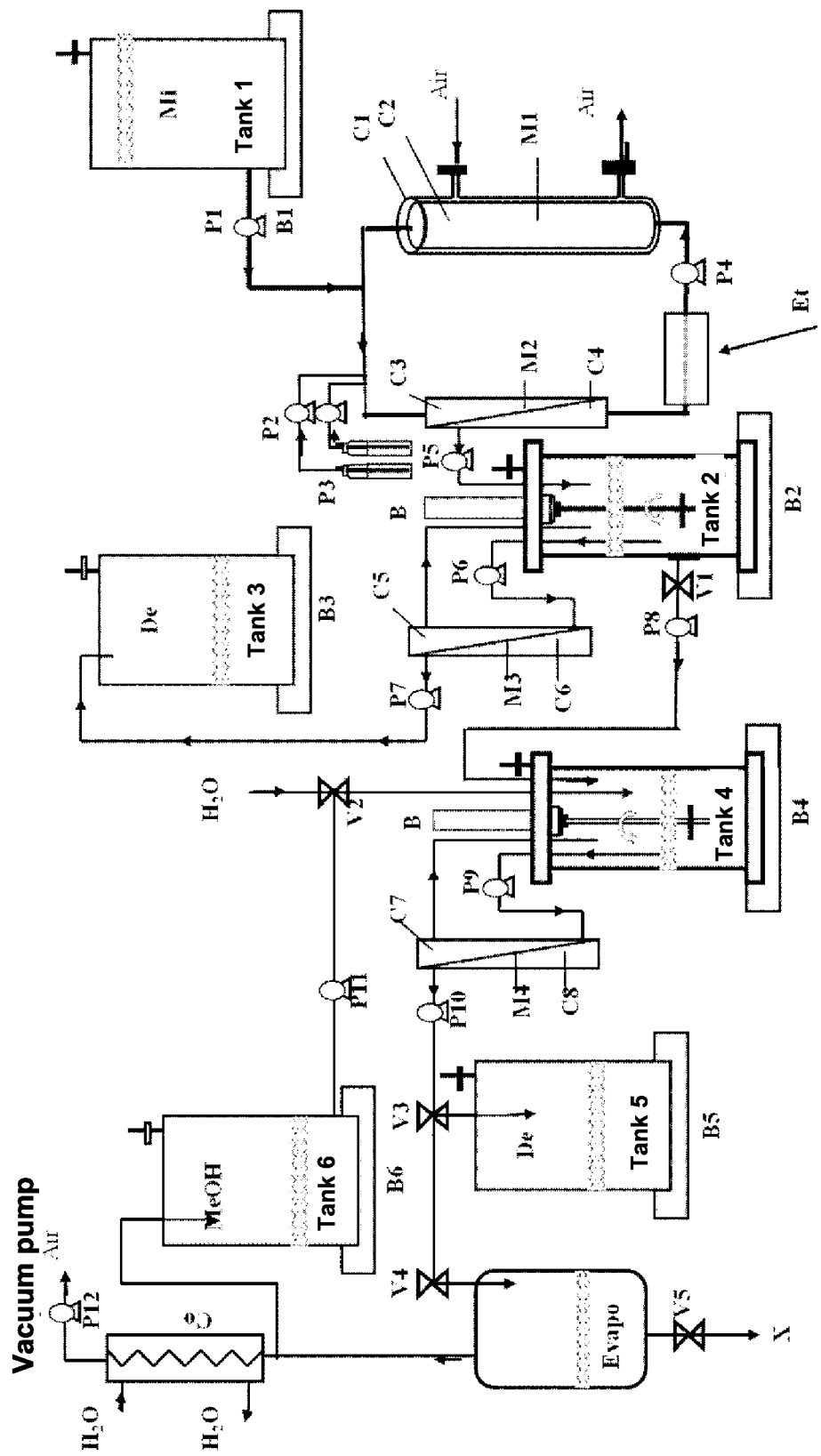
FIG. 2 is a diagram representing a device for the continuous production, without the formation of foam, the extraction and the purification of the lipopeptides produced by a microorganism. In this figure, C1, C2, C3, C4, C5, C6, M1, M2, M3, B1, B2, B3, P1, P2, P3, P4, P5, P6, P7, "Mi", "De" and "Et" have the same meaning as for FIG. 1. M4 represents the ultrafiltration membrane of an ultrafiltration means having the compartments C7 and C8. B4, B5, B6 and B7 each represent scales. B represents a motor for driving a stirring means in the dish 2 or the dish 4. P8, P9, P10, P11 and P12 represent volumetric pumps. V1, V2, V3, V4 and V5 represent valves. "Co" signifies "condenser" and "X" corresponding to a liquid solution comprising the lipopeptides produced by the microorganism.
Figure 3:
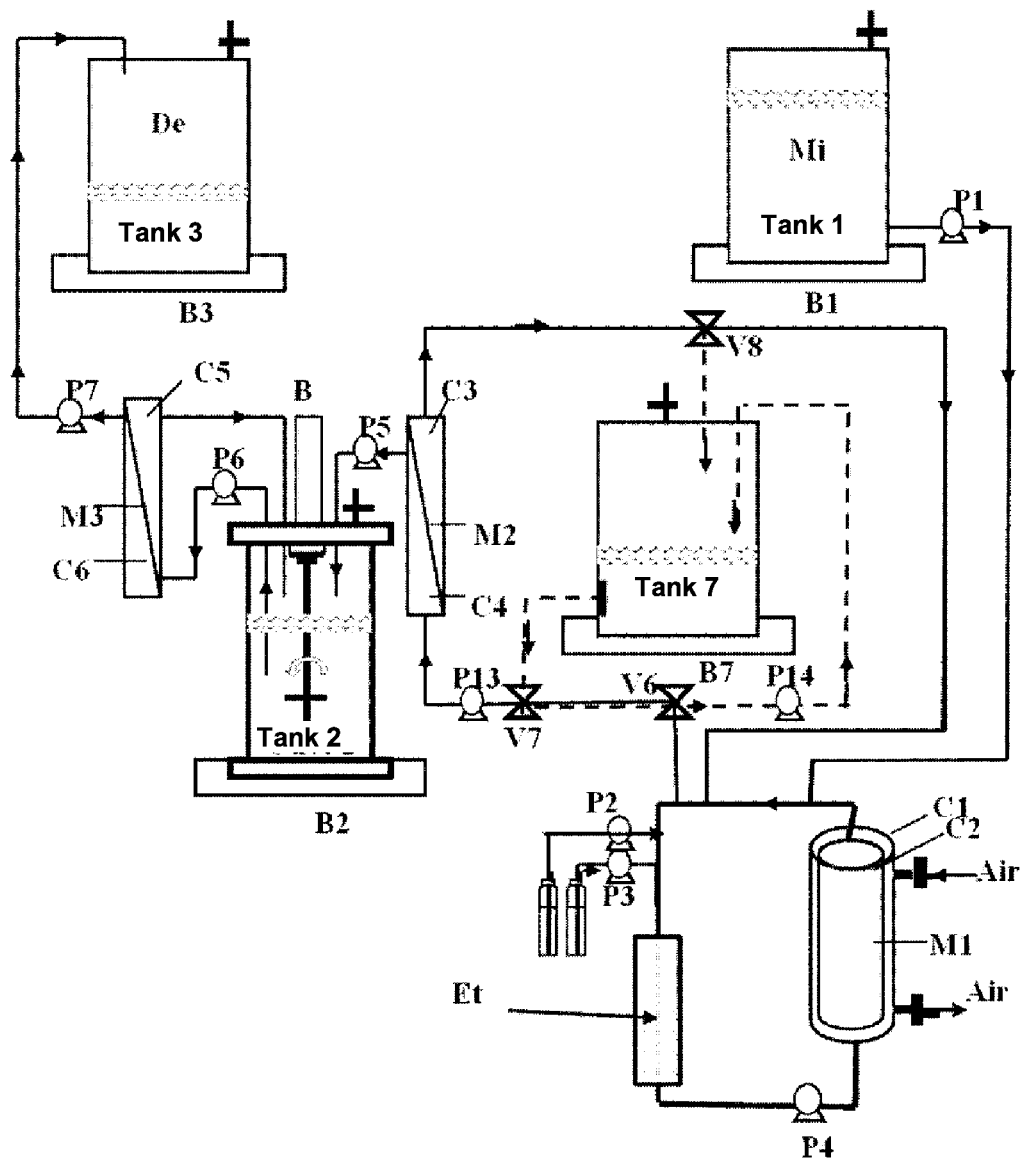
FIG. 3 is a diagram representing the device of FIG. 1 in which an alternative circuit is shown in broken lines. P13 and P14 represent volumetric pumps. V6, V7 and V8 represent valves. B7 represents scales.
Figure 4:
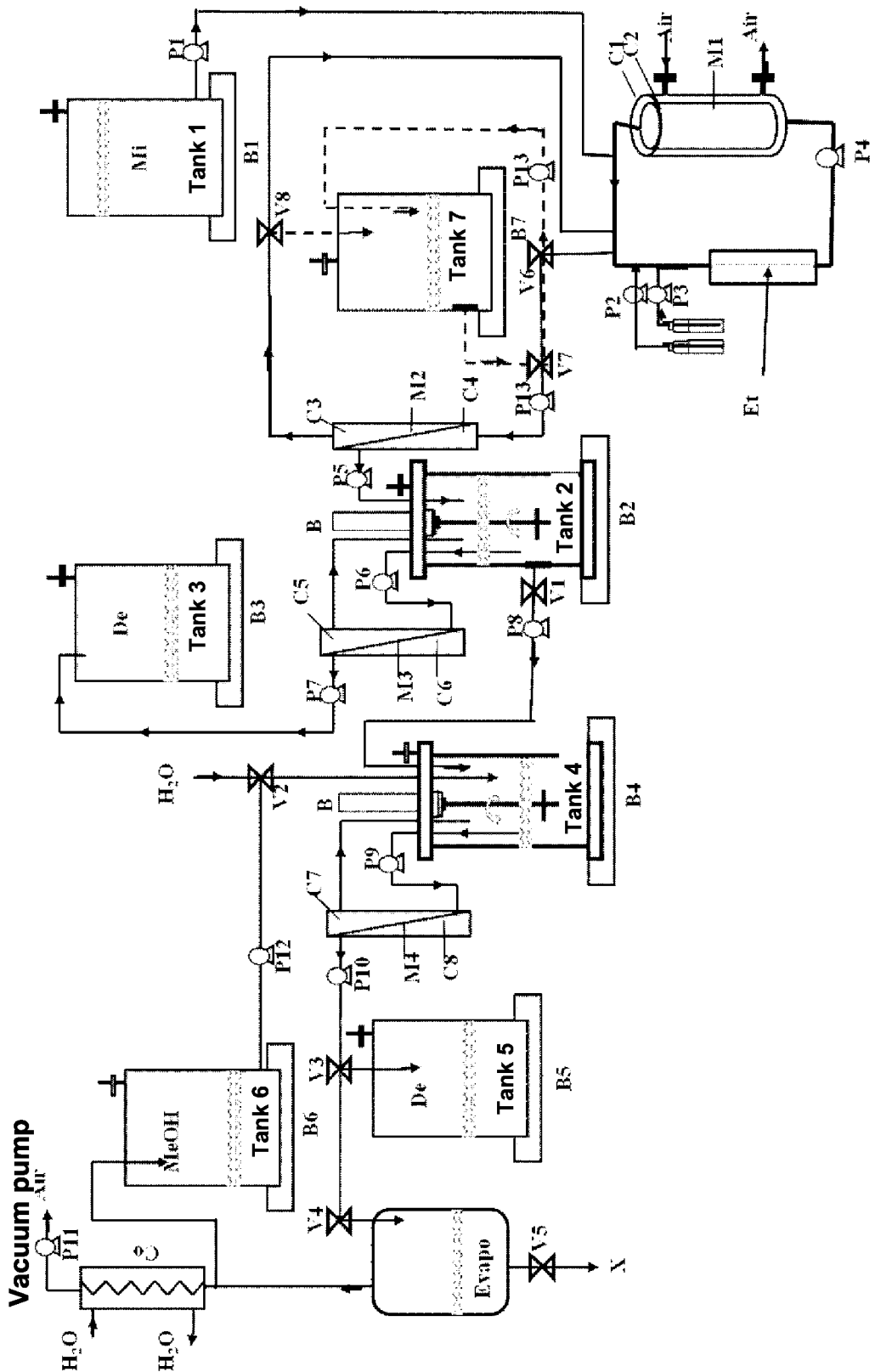
FIG. 4 is a diagram representing the device of FIG. 2 in which an alternative circuit is shown in broken lines. P13 and P14 represent volumetric pumps. V6, V7 and V8 represent valves. B7 represents scales.
Figure 5:
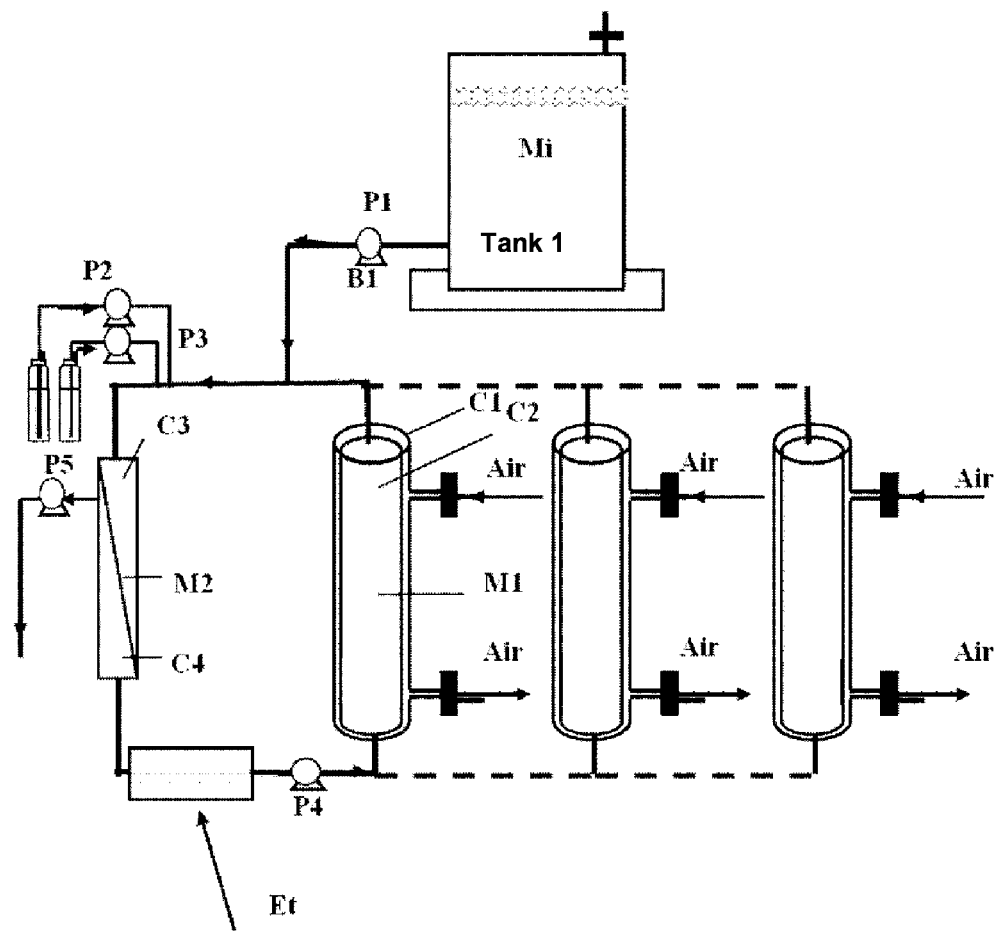
FIG. 5 shows the first parts of the device described in FIGS. 1 to 4, in which there is a plurality of air/liquid contactors that are disposed in parallel. In this diagram, three air/liquid contactors are shown.

Example 1: Construction of the Bacillus subtilis BBG125 Strain

The Bacillus subtilis BBG125 strain was filed on 10 Mar. 2011 under the number CNCM 1-4451 in the National Collection of Microorganism Cultures (CNCM) of the Institut Pasteur (Paris, France).

It was constructed from the Bacillus subtilis strain of the ATCC 6633 wild type (Duitman et al, 1999. The mycosubtilin synthetase of Bacillus subtilis ATCC 6633: a multifunctional hybrid between a peptide synthetase, an amino transferase, and a fatty acid synthase. Proc. Natl. Acad. Sci. USA, 96, 13294-13299 [12]) according to the protocol described below.

1.1 Protocol for Constructing the pBG200 Hybrid Plasmid containing εpbp-P$_{repU}$-neo-εfenF and rep(R6K)

The pBG106 plasmid (Lecléreet al, 2005. Mycosubtilin overproduction by Bacillus subtilis BBG100 enhances the organism's antagonistic and biocontrol activities. Appl. Environ. Microbiol., 71, 4577-4584 [13]), was digested by the restriction enzymes SphI (Fermentas, Villebon sur Yvette, France; reference ER0601) and SacI (Fermentas, Villebon sur Yvette, France; reference ER1131) in order to isolate and purify a fragment εpbp-P$_{repU}$-neo-εfenF of 2.6 kilo-pairs of bases (kb) of sequence SEQ ID NO: 11, in accordance with the protocol described in: Sambrook and Russell, 2001. Molecular cloning: a laboratory manual, 3$^{rd}$ ed., Cold Spring Harbor Laboratory, Cold Spring Harbor, N.Y. [14].

This sequence carries two cassettes (εpbp and εfenF) for performing homologous recombinations with the chromosome of the Bacillus subtilis ATCC 6633 strain.

At the same time, the plasposon pTnMod-RKm' (Dennis and Zylstra, 1998. Plasposons: modular self-cloning mini-transposon derivatives for rapid genetic analysis of gram-negative bacterial genomes. Appl. Environ. Microbiol. 64, 2710-2715 [15]) was treated by the restriction enzymes Nspl (Fermantas, Villebon sur Yvette, France; reference ER1471) and SacI (Fermentas, Villebon sur Yvette, France; reference ER1131) generating a mixture of five fragments, including the fragment carrying rep(R6K) of 451 pairs of bases (pb), the sequence of which has been isolated and purified (Sambrook and Russell, 2001 [14]).

The fragments containing the sequences εpbp-P$_{repU}$-neo-εfenF and rep(R6K) were then ligatured together and (Sambrook and Russell, 2001 [14]).

The sites of the restriction enzymes used were as follows:
Sphl: GCATGC (in position 1 of the sequence SEQ ID NO: 11)
Xbal: TCTAGA (in positions 743 and 2088 of the sequence SEQ ID NO: 11) and
SacI: GAGCTC (in position 2630 of the sequence SEQ ID NO: 11)

The cassettes εpbp, P$_{repU}$-neo and εfenF were composed in the following manner:
cassette εpbp: from Sphl to Xbal (SEQ ID NO: 12),
cassette P$_{repU}$-neo: from Xbal to Xbal (SEQ ID NO: 13),
cassette εfenF: from Xbal to Sacl (SEQ ID NO: 14).

The ligature obtained was used to transform the stain of Escherichia coli CC118(λpir) (Herrero, de Lorenzo and Timmis, 1990. Transposon vectors containing non-antibiotic resistance selection markers for cloning and stable chromosomal insertion of foreign genes in gram-negative bacteria. J. Bacteriol. 172: 6556-67 [16]) with a selection on a Luria-Bertani medium (or LB or Luria Broth medium) (Bertani, 2003, Lysogeny at mid-twentieth century: P1, P2 and other experimental systems. J. Bacteriol. 186, 595-600 [17]) containing 20 µg/ml of neomycin. The plasmid obtained at E. coli(λpir) was called pBG200 (3.1 kb)

Figure 6:
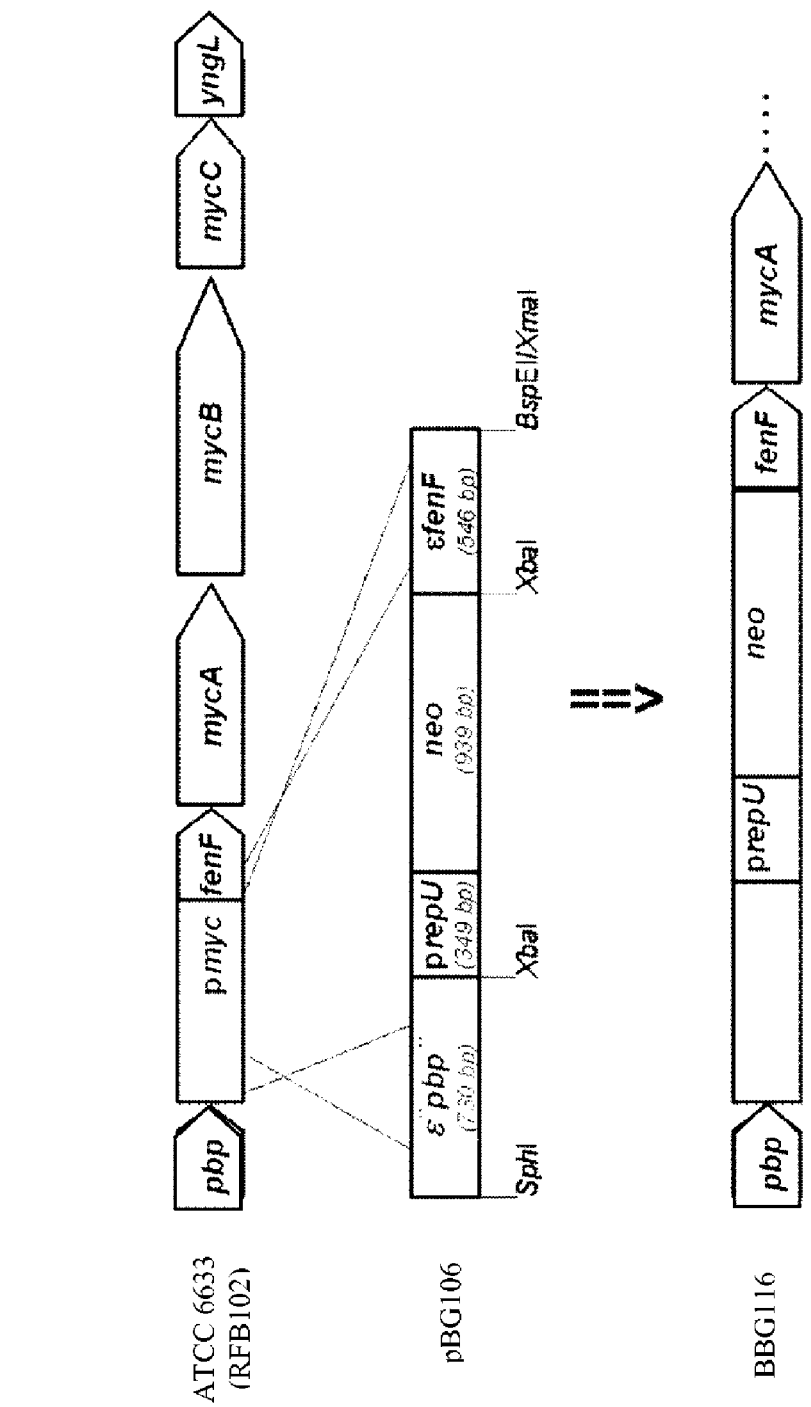
FIG. 6 is a schematic representation of the homologous recombination of a fragment of 2.6 kb, bearing the sequence εpbp-P$_{repU}$-neo-εfenF of the pBGB106 plasmid, the fragments εpbp and εfenF issue by PCR from Bacillus subtilis ATCC 6633, thus forming the plasmid pBG200. In this figure, "Sphl, "XbaI", "BspEI" and "XmaI" represent the restriction sites of the respective eponymous enzymes. "εpbp" and "εfenF" represent cassettes for homologous recombination. "pbp" represents the gene coding for a protein bonding to penicillin. "P$_{myc}$" represents the original promoter of B. subtilis ATCC 6633. "fenF", "mycA", "mucB" and "mycC" represent the four genes that constitute the operon of mycosubtilin. "yngL" represents the gene coding for a protein having an unknown function. "P$_{repU}$" represents the promoter of the replication gene of pUB110. "neo" represents a gene conferring resistance to neomycin/kanamycin.

FIG. 6 shows this construction schematically.

1.2 Protocol for Obtaining BBG116

The strain B. subtilis RFB102 (the strain derived from B. subtilis ATCC 6633 obtained by insertion of the Pspac-comK cassette in amyE. Pspac designates the promoter issuing from the plasmid pA-spac (Bacillus Genetic Stock Center, Columbus, Ohio, USA) inducible by IPTG, comK designates a gene essential for natural competence in Bacillus. It is associated with a gene for resistance to spectinomycin (Pspac-comk-spc), which is integrated in the chromosome gene amyE. The strain RFB103 has increased ability for transformation by natural competence, which is induced by IPTG (isopropyl-β-D-galactopyranoside). It was transformed by pBG200 previously treated by the plasmid amplification system TempliPhi (GE Healthcare), and then selected by means of resistance to neomycin, according to the protocol described in Dubnau, 1982 (Genetic transformation of *Bacillus subtilis* p148-178. In D. Dubnau (Ed) The molecular biology of the Bacilli, vol. I. *Bacillus subtilis*. Academic Press, Inc. New York [18]).

Among the Nm-R clones, the insertion by double crossing-over of the cassette εpbp-P$_{repU}$-neo-εfenF in the chromosome of RFB102 was verified by PCR using the primers

```
                                     (SEQ ID NO: 1)
PBP-FO2:
AATAACGGACATGCCGAAGTG
and FENF-REF2:
                                     (SEQ ID NO: 2)
AATAGGCCGACCAAGACGTTC.
```

The overproduction of mycosubtilin in a Landy/MOPS medium at 22° C. was verified in accordance with the operating method described in example 2 below.

The strain *B. subtilis* BBG116 was thus obtained.

1.3 Protocol for Constructing the pBG144 Plasmid

A pBG212 plasmid of 6.5 kb dedicated to the insertional inactivation ("knock-out") of the srfA operon of *B. subtilis* was constructed as follows:

A εsrfAA (2.2 kb) cassette was generated by PCR using primers SRF-FO ACAGGAATATGCTCAATCGAAG (SEQ ID NO: 3) and SRF-REV AAATTCGCTTCCAGGCTTCTG (SEQ ID NO: 4), from the genome DNA of *B. subtilis* subsp. *subtilis* strain 168 (Accession NCBI PRJNA76) previously inserted in the plasmid pGEN=T Easy (Promega Corp, Charbonnières, France).

This amplicon was subsequently sub-cloned in the site EcoRI (Fermentas, Villebon sur Yvette, France; reference ER0271) of the vector pUC19 (New England Biolabs, Ispwich, Mass., USA).

The εsrfAA cassette was then interrupted at the site MfeI (Fermentas reference ER0751) by insertion of the tet gene, previously generated by PCR using the primers TETP1 GTTGTATCGATGATGAAATACTGAATTTTAAACTTAG (SEQ ID NO: 5) and TETT1 TTTAATGGATCTAGAAGATTTGAATTCCTGTTAT (SEQ ID NO: 6), from the plasmid pBC16 (DSMZ GmbH, Brunswick, Germany), the originator of *Bacillus cereus* (Accession: NC_001705.1).

The plasmid pBG144 was obtained by insertion, at the site BstEII (Fermentas, Villebon sur Yvette, France; reference ER0391) situated at the end of the gene tet, of the gene cat previously generated by PCR using the primers pC194cmfwd AGAAAGCAGACAGGTAACCCTCCTAA (SEQ ID NO: 7 and pC194cmrev GCAGGTTAGTGACATTAGGTAACCGA (SEQ ID NO: 8) of the plasmid pC194 originating from *Staphylococcus aureus* (DSMZ GmbH, Brunswick, Germany, Accession: NC_002013.1).

Figure 7:
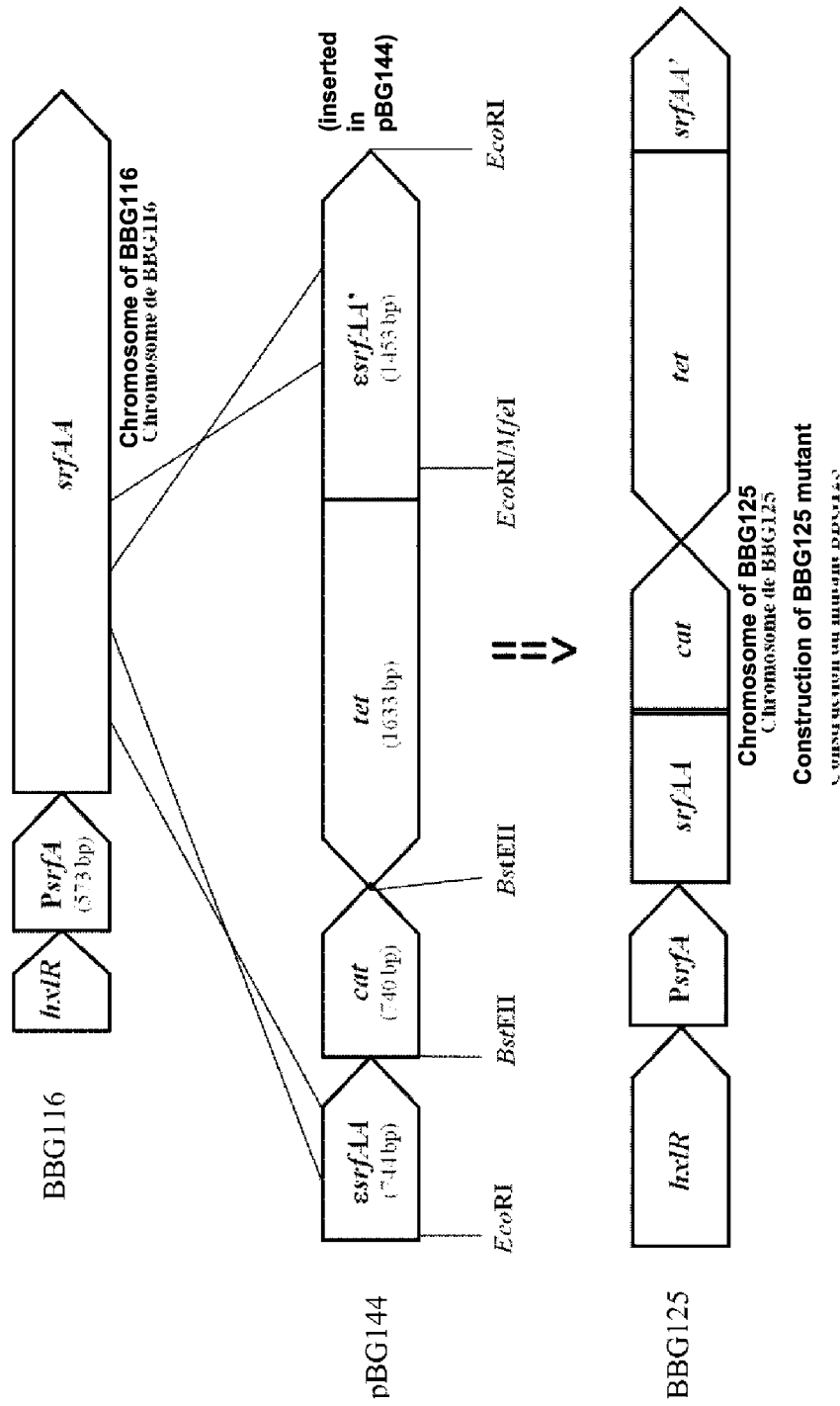
FIG. 7 is a schematic representation of the homologous recombination of a pBG144 plasmid at the srfA operon of the BBG116 strain, leading the BBG125 strain. "EcoRi", "BstEII" and "MfeI" represent the restriction sites of the respective eponymous enzymes. "εsrfAA" and "εsrfAA'" represent cassettes for homologous recombination. "hxlR" represents a gene situated upstream of the srfA operon. "P$_{srfA}$" represents the native promoter of the srfA operon. "cat" represents the gene for resistance to chloramphenicol. "tet" represents a gene for resistance to tetracyclin.

FIG. 7 shows this construction schematically.

1.4 Protocol for Obtaining *B. subtilis* BBG125

Novel transformations of *B. subtilis* BBG116 with the plasmid pBG144 previously linearised by AatII (Fermentas, Villebon sur Yvette, France; reference ER0991) in accordance with the protocol described in Dubnau, 1982 (Genetic transformation of *Bacillus subtilis* p148-178. In D. A. Dubnau (Ed) The molecular biology of the Bacilli, vol I. *Bacillus subtilis*. Academic Press, Inc. New York [18]).

Six Cm-R Tc-R clones were isolated on a gelosed LB medium containing the appropriate antibiotics. Checks by PCR were carried out using the primers SRFAA5-FWD; AAGGAATCTCGCAATCATTTATCG (SEQ ID NO: 9) and SRFAA5REV; CTTGGTGTAAGCGGAATTTCTGTC (SEQ ID NO: 10). The non-production of surfactin in a Landy/MOPS medium at 37° C. was verified in accordance with the operating method described in example 2 below.

The mutant *B. subtilis* BBG125 was adopted as a monoproducing strain of mycosubtilin.

The two strains *B. subtilis* BBG116 and BBG125 have haemolytic activities on gelose containing 5% blood as well as antifungal activities on yeasts and moulds on a PDA medium.

These activities are more marked in the case of the strain *B. subtilis* BBG 116, because of the synergy between the surfactant produced and an overproduction of mycosubtilins. These properties are in close relationship with their ability to colonise the surface of the gelosed media, by virtue of the reduction in their surface tension.

The summarised characteristics of *B. subtilis* BBC125 and its parental strains are presented in table 1 below:

TABLE 1

Summarised characteristics of *B. subtilis* BBG125 and its parental strains

| *B. subtilis* | Parent strain | Genotype | Phenotype |
|---|---|---|---|
| ATCC 6633 | — | Wild | Com$^-$Myc$^+$ Srf$^+$ |
| RFB102 | ATTC 6633 | amyE::Pspac-comK-spc | Com$^{++}$ Amy$^-$ Myc$^+$ Srf$^+$ Spc$^R$ |
| BBG116 | RFB102 | amyE::Pspac-comK-spc, myc::P$_{repU}$-neo | Com$^{++}$ Amy Myc$^+$ Srf$^+$ Spc$^R$ Nm$^R$ |
| BBG125 | BBG116 | amyE::Pspac-comK-spc, myc::P$_{repU}$-neo, srfAA::cat-tet | Com$^{++}$ Amy Myc$^+$ Srf$^-$ Spc$^R$ Nm$^R$ Tc$^R$ Cm$^R$ |

[Com: natural competence for transformation; Myc: production of mycosubtilin; Srf: production of surfactin; Amy: amylolytic activity; Spc$^R$ Nm$^R$ Tc$^R$ Cm$^R$: resistances to spectinomycin, neomycin/kanamycin, tetracylin and chloramphenicol, respectively]

In comparison with the strain *Bacillus subtilis* ATCC 6633, the strain *Bacillus subtilis* BBG125 produces a larger quantity of mycosubtilins and does not produce any surfactin.

Example 2: Preparation of the Culture Media 2.1 The Landy Medium

The composition of the Landy medium is as follows: glucose, 20 g/l; glutamic acid, 5 g/l, yeast extract, 1 g/l; $K_2HPO_4$, 1 g/l; $MgSO_4$, 0.5 g/l; KCl, 0.5 g/l; $CuSO_4$, 1.6 mg/l; $Fe_2(SO_4)_3$, 1.2 MG/l; $MnSO_4$, 0.4 mg/l.

2.2 Stock Solutions

In order to ensure reproducibility of the composition of the medium, sterile concentrated solutions were produced. A solution of 10× glucose (200 g/l) was sterilised by autoclaving at 121° C. for 20 minutes. A solution of 4× glutamic acid (20 g/l) was adjusted to pH 8 with a solution of 5M KOH and was sterilised by filtration on a filter with a porosity of 0.2 µm. A 20× yeast extract solution (20 g/l) was sterilised by autoclaving at 121° C. for 20 minutes. A solution of 40× n° 1 minerals ($K_2HPO_4$, 40 g/l; $MgSO_4$, 20 g/l; KCl, 20 g/l) was acidified with concentrated $H_2SO_4$ to total dissolution of the salts and were sterilised by filtration on a 0.2 µm filer. A solution of 40× n° 2 mineral salts ($CuSO_4$, 64 mg/l; $Fe_2(SO_4)_3$, 48 mg/l; $MnSO_4$, 16 mg/1) was acidified with concentrated sulphuric acid to total dissolution of the salts and was sterilised by filtration on a filter with a porosity of 0.2 µm.

2.3 Production of One Liter of Landy Medium

The material used, apart from the pipettes, which are sterile and for single use, was previously sterilised by autoclaving at 121° C. for 20 minutes, 250 ml of the glutamic acid solution was taken off in a sterile fashion and was then poured into an Erlenmeyer flask. 100 ml of the glucose solution was added thereto in a sterile fashion, and then 50 ml of the yeast extract solution and finally 25 ml of each of the mineral solutions. The pH was adjusted to 7.0 by means of a sterile 5M KOH solution. The volume was supplemented to 1 liter with sterile water.

2.4 Production of a Landy Medium Buffered with 200 mM of MOPS

A 20×MOPS buffer (2M) was produced by dissolving 20.93 g of 3-[N-Morpholino]propanesulfonic acid (MOPS) (M1254, Sigma, St Louis, Mo., USA) in 50 ml of water. The solution was sterilised on a filter with a porosity of 0.2 µm under a laminar-flow hood. To produce 1 liter of Landy medium buffered to 100 mM with MOPS, 50 ml of 20×MOPS was added to the mixture produced in example 2.3.

Example 3: Culture of *B. subtilis* BBG125 in Erlenmeyer Flasks 3.1 Preparation of a Strain Collection A screw-type tube containing 5 ml of modified E medium (the Clark E medium is modified by reducing the glucose concentration from 40 to 20 g/l. The composition of the medium is as follows: $KH_2PO_4$, 2.7 g/l; $K_2HPO_4$, 18.9 g/l; yeast extract, 0.5 g/l; glucose, 20 g/l; EDTA, 0.05 g/l; $MgSO_4$, 0.61 g/l; $MnSO_4$, 0.056 g/l; NaCl, 0.1 g/l; $CaCl_2$, 0.012 g/l; $ZnZO_4$, 0.018 g/l; $FeSO_4$, 0.018 g/l; $CuSO_4$, 0.002 g/l; $Na_2MoO_4$, 0.001 g/l; $H_3BO_3$, 0.001 g/l; $Na_2SO_3$, 0.001 g/l; $NiCl_2$, 0.0037 g/l; $NH_4NO_3$, 4 g/l; $MgSO_4$, 1 g/l. The pH of the solution is adjusted to 6.5 with a 10% HCl solution) was inoculated with a colony of the primary strain collection of *B. subtilis* BBG125 and set to incubate at 30° C. for 24 hours under a stirring of 300 rotations per minute (rpm). The solution was then homogenised by vortex. A volume of 1.5 ml of the culture obtained previously was added to 48.5 ml of modified E medium contained in a 500 ml Erlenmeyer flask. The whole was set to incubate at 30° C. for 12 to 24 hours under stirring of 120 rpm. This first preculture P1 was duplicated.

The culture was then homogenised by vortex, and the $DO_{600\ nm}$ was then measured with a spectrophotometer (SECOMAN Prim, SECOMAN, Domont, France) until the *B. subtilis* BBG125 strain was at the start/middle of an exponential growth phase.

A P2 preculture was inoculated with 0.5 ml of the culture of the best flask P1 and was duplicated. The 500 ml Erlenmeyer flasks contained, as the final volume, 50 ml of modified E medium and were incubated at 30° C. under 120 rpm stirring. The growth was stopped when the $DO_{600\ nm}$ indicated that the culture was at the start/middle of an exponential growth phase ($1<DO_{600\ nm}<5$). The purity and quality of P2 were checked, by observation with a microscope and by seeding with a nutritive Luria-Bertani gelose (Tryptone, 10 g/l; yeast extract, 5 g/l; NaCl, 10 g/l; pH 7.2 and a Mossel gelose (meat extract, 1 g/l; peptone, 10 g/l; D-mannitol, 10 g/l; NaCl, 10 g/l; phenol red, 0.025 g/l, agar, 12 g/l; egg yolk, 10 ml/l; polymyxin, 5 ml/l; pH 7.1)), more specific of the bacilli, complemented with spectinomycin at 100 µg/ml. The dishes were set to incubate at 30° C. for 24 hours.

It should be noted that *B. subtilis* produces colonies with irregular shapes (the contours are undulating and may exhibit filaments), with a creamy consistency, the diameter of which is between 2 and 4 mm. In old cultures, the colonies adopt a dry, rough appearance and become encrusted in the gelose.

Finally, a 2 liter flask containing 200 ml of modified E medium defined above was inoculated at 5% with the best flask of P2. This flask was incubated at 30° C. under stirring of 120 rpm and the growth was stopped when the $DO_{600\ nm}$ indicated that the culture is at the start/middle of an exponential growth phase ($1<DO_{600\ nm}<5$). The quality and purity of the culture were checked as indicated for P2. The culture was centrifuged at 2000 g for 10 minutes at 25° C. The residues were washed in sterile physiological water and then the suspensions were centrifuged at 2000 g for 10 min at 25° C. The residues were taken up in a volume of E medium without antibiotic, so as to obtain a final $DO_{600\ nm}$ of 25 per tube. The suspension was distributed in cryotubes at the rate of 0.9 ml of culture and 0.6 ml of glycerol. The tubes were homogenised by vortex and stored at −80° C. The E medium was supplemented with spectinomycin at 100 µg/ml.

3.2 Preparation of an Inoculum

The inoculum was prepared from the strain collection containing cells kept at −80° C. in 40% glycerol. A tube containing 5 ml of modified E medium defined below was adjusted to pH 7.0 with a 10% HCl solution (v/v) and was inoculated with 0.5 ml of bacterial suspension of the strain collection. The whole was set to incubate at 30° C. for 10 to 14 hours under stirring of 300 rpm. The tube was then homogenised by vortex and the $DO_{600nm}$ was measured. A preculture P1 is then produced in a final volume of 50 ml of modified E medium at pH 7.0 contained in a 500 ml Erlenmeyer flask. The whole was set to incubate at 30° C. under stirring of 140 rpm, the preculture was stopped when the strain was situated at the start/middle of an exponential growth phase ($1<DO_{600\ nm}<5$). This first preculture P1 was duplicated.

A second preculture P2 was produced in the same way as the preculture P1 and this was inoculated from the first flask of P1 and was duplicated. The volume necessary for starting the cultures in flasks was then centrifuged at 2000 g for 10 min at 25° C. The residue was put back in suspension in 10 ml of sterile physiological water. The suspension obtained was centrifuged once again at 2000 g for 10 min. The residue was finally taken up in 10 ml of sterile physiological water. The suspension was then ready for inoculation.

3.3 Cultures in Erlenmeyer Flasks

The experiments lasted for a minimum of 72 hours and several samples were taken from these cultures. The initial $DO_{600\ nm}$ is between 0.1 and 0.4. The volume of the Erlenmeyer flasks was 500 ml and the volume of the nutritive medium was 100 ml. The following measurements were performed on the samples taken in a sterile fashion under the laminar-flow hood: a check on the purity by isolation on nutritive gelose and Mossel gelose+spectinomycin (100 µg/ml), a measurement of the optical density at 600 nm, a measurement of the pH, a measurement of the dry weight and the taking off of the culture supernatant for quantitative analysis of the lipopeptides by HPLC: 3 ml of culture is centrifuged for 10 minutes at 10,000 g at 4° C. and the culture supernatant was stored at −20° C.

Example 4: Purification and Analysis of the Lipopeptides 4.1 Purification of the Lipopeptides The lipopeptides were extracted on cartridges of 1 g of Maxi-clean C18 gel (Grace Davison-Alltech, Deerfield, Ill., USA).

A cartridge of 1 g of ODS was conditioned with 100% methanol, with 20 ml at the first pass and then 8 ml. The cartridge was then rinsed with 8 ml of milli-Q water (Millipore). 1 ml of culture supernatant with a pH of 6.5±0.1 was then loaded onto the column. The cartridge was then washed with 8 ml of milli-Q water. After drying of the cartridge with 20 ml of air, the lipopeptides were eluted with 4 ml of 100% methanol. The eluate was dried by means of a vacuum concentrator. The sample was subsequently taken up in 200 µl of 100% methanol at 4° C. to enable HPLC analysis.

4.2 Analyses by High Performance Liquid Chromatography (HPLC)

The sample was analysed by means of a complete HPLC system, make Waters (Online Degasser, 717 Autosampler, 660S Controller, 626 Pump, 2996 PhotoDiodeArray) (Waters SAS, Guyancourt, France) using a C18 column (5 µm, 250×2.5 mm, VYDAC 218 TP). Two analyses were carried out.

The first analysis was that of the mycosubtilins: 10 µl of purified sample was injected and compared with an iturin A standard at 500 mg/min (11774, Sigma-Aldrich, St Louis, Mo., USA) with a flow rate of 0.6 ml/min. The elution was carried out in isocractic mode using a 60/40/0.1 (v/v/v) water/acetonitrile/trifluoroacetic acid solvent.

The second analysis was that of the surfactins. 10 µl of purified sample was injected compared with a surfactin standard at 500 mg/l (S3523, Sigma-Aldrich, St Louis, Mo., USA) with a flow rate of 0.6 ml/min. The elution was carried out in isocratic mode using a 20/80/0.1 (v/v/v) water/acetonitrile/trifluoroacetic acid solvent.

The retention time and the second drift of the spectrum between 200 and 400 nm of each peak (diode array, PDA 2996, Waters) were analysed automatically by means of Millennium software for identifying the eluted molecules.

4.3 Analyses by Semi-Preparative HPLC

The sample was prepared by applying the purification protocol described in example 4.1 above, using cartridges of Maxi-clean C18 gel (Grace Davison-Alltech, Deerfield, Ill., USA) of 10 g. The use of 10 g cartridges made it possible to load 10 ml of culture supernatant instead of 1 ml as before. All the volumes were multiplied by a factor of 10, except for the volumes of methanol. The minimum volume of methanol used for conditioning the cartridge and then eluting the lipopeptides was 10 ml. The sample was loaded manually (100 µl) into the injection system of the semi-preparative HPLC, make Waters (660 Controller, 626 Pump, 486 Absorbance Detector). The column used was a C18 (5 µm, 300×10 mm, ACE). The elution was carried out at a rate of 3 ml/min in accordance with the gradient presented in table 2 below:

TABLE 2

Elution according to the respective concentrations of buffers A and B

| Time (min | Buffer A (%) | Buffer B (%) |
|---|---|---|
| 0 | 65 | 35 |
| 4 | 65 | 35 |
| 54 | 50 | 50 |
| 60 | 0 | 100 |
| 61 | 65 | 35 |
| 65 | 65 | 35 |

The solvents used are as follows: solvent A composed of water and trifluoroacetic acid, 99.9/0.1 (v/v) and solvent B composed of acetonitrile and trifluoroacetic acid, 99.9/0.1 (v/v).

4.4 Analyses by MALDI-TOF Mass Spectrometry

The analyses by MALDI-TOF mass spectrometry (Bruker Ultaflex) were carried out according to requirements using: either culture supernatants, or samples purified on ODS cartridge (Grace Davison-Altech, Deerfield, Ill. USA) or samples purified on ODS cartridge and by semi-preparative HPLC. A TA buffer was prepared by producing a 33/67/0.1 (v/v/v) $CH_3CH$/water/trifluoroactic acid mixture. A CHCA buffer is a saturated solution of alpha-cyano-4-hydroxycinnamic acid in TA buffer. This buffer was prepared by recovering the supernatant after centrifugation of the alpha-cyano-4-hydroxycinnamic acid/TA buffer. The samples to be analysed were prepared by mixing 1 µl sample with 9 µl of HCA buffer. The solution of sample deposited by MALDI-TOF analysis represented a volume of 0.5 µl. Drying was carried out in open air. The masses were calibrated with a mixture of standard peptides.

The calculated masses of the ions $[M+H]^+$, $[M+Na]^+$, $[M+K]^+$ of the various homologues of mycosubtilins and surfactins obtained are specified in table 3 below:

TABLE 3

Calculated masses of the $[M + H]^+$, $[M + Na]^+$, $[M + K]^+$ ions of the various homologues of mycosubtilins and surfactins

| Lipopeptides | Masses | | |
|---|---|---|---|
| | $[M + H]^+$ | $[M + Na]^+$ | $[M + K]^+$ |
| Surfactin $C_{13}$ | 1008.66 | 1030.64 | 1046.61 |
| Surfactin $C_{14}$ | 1022.67 | 1044.66 | 1060.63 |
| Surfactin $C_{15}$ | 1036.69 | 1058.67 | 1074.65 |
| Mycosubtilin $C_{15}$ | 1057.57 | 1079.55 | 1095.52 |
| Mycosubtilin $C_{16}$ | 1071.58 | 1093.56 | 1109.54 |
| Mycosubtilin $C_{17}$ | 1085.60 | 1107.58 | 1123.55 |

The HPLC analysis revealed 10 peaks for which the molecular masses of the molecules detected are presented in table 4 below:

TABLE 4

Masses of the 10 peaks detected by HPLC analysis

| Peak N° | Mass |
|---|---|
| 1 | 1056 |
| 2 | 1084 |
| 3 | 1084 |
| 4 | 1070 |
| 5 | 1070 |
| 6 | 1098 |
| 7 | 1098 |
| 8 | 1084 |

TABLE 4-continued

Masses of the 10 peaks detected by HPLC analysis

| Peak N° | Mass |
|---------|------|
| 9 | 1084 |
| 10 | 1098 |

4.5 Analyses of the Structure of the Novel Mycosubtilins by MS-MS

In order to precisely determine the structure of the various forms of mycosubtilin produced by the BBG125 strain, an analysis of the purified samples was carried out by tandem mass spectrometry (MS-MS) with ionisation of the electrospray type (Ion Trap Finnigan MAT LCQ) in direct infusion mode after starting the peptide cycle by means of a treatment with N-bromosuccinimide in a concentration equivalent to mycosubtilin in a 70% acetic acid solution.

A first analysis was carried out on the purified C17 anteiso mycosubtilin (peak 8). The spectrum obtained (MS1) is complicated by the two isotopes of Br. The spectrum MS2 is complicated by the presence of fragments with 1, 2 or 3 —$NH_3$ groups missing, owing to the presence of the Asn and Gln amino acids. The MS spectrum of the starting product gives the peaks 1085 $[M+H]^+$, 1107 $[M+Na]^+$ and 1123 $[M+K]^+$ corresponding clearly to C17 mycosubtilin.

Because of the presence of the isotopes 79BR and 81Br in fairly similar quantities, a distribution of peaks around 1260 is observed that do indeed correspond to the expected drift. For example, the peak at 1257.4 corresponds to $[M+H]^+$ with two 79Br, the peak at 1259.4 corresponds to $[M+H]^+$ with 79Br and 81Br or to $[M+H]^+$ with two 13C and two 79Br, etc.

The order of the increasing masses obtained from the fragmentation of the ion at 1257.4 is set out in table 5 below:

TABLE 5

Increasing masses obtained from the fragmentation of the ion at 1257.4

| m/z | Ion fragment |
|-----|--------------|
| 365 | Vn-$NH_3$ |
| 382.4 | vN |
| 391.6 | b4-$H_2O$—$NH_3$ |
| 432 | y2-$NH_3$ |
| 434.4 | SNv-$H_2O$—$NH_3$ |
| 452.3 | Snv-$NH_3$ |
| 462.3 | NvN—$2NH_3$ |
| 496.4 | NvN |
| 506.2 | b5-$2NH_3$ |
| 531.3 | SNvN-$H_2O$—$2NH_3$ or PSNV-$H_2O$—$NH_3$ |
| 549.4 | SNvN—$2NH_3$ or PSNv-$NH_3$ |
| 566.3 | PSNv or SNvN—$NH_3$ |
| 583.4 | SNvN |
| 700 | Y3—$NH_3$ |
| 717.1 | y3 |
| 814.0 | y4-$NH_3$ |
| 831.1 | y4 |
| 918 | y5 |
| 664 | y6-$3NH_3$ |
| 981.1 | y6-$2NH_3$ |
| 998.1 | y6-$NH_3$ |
| 1015.1 | y6 |
| 1091.9 | Y7—$3NH_3$ |
| 1109.1 | Y7—$2NH_3$ |
| 1126.0 | y7-$NH_3$ |
| 1143 | y7 |
| 1420.0 | M-$H_2O$ |

In the above table, "m/z" means mass to charge ratio.

4.6 MS-MS Analysis of the Peak at 1274.4 Contained in Peak 6

Isotope mass before treatment: M=1098.6

Isotope mass after treatment, with 79BR2: M=1270.4

Fragment y identical to $C_{17}$ anteiso mycosubtilin.

Fragments b greater than 14 with respect to the fragments b of $C_{17}$ anteiso mycosubtilin.

This means that very probably one of the first two amino acids in the open sequence (N or Q of NQPSNvNw) has been modified.

4.7 MS/MS Analysis of the Peak at 1274.4 Contained in Peak 10

Isotope mass before treatment: M=1098.6

Isotope mass after treatment, with 79Br1: M=1270.4

Fragments y identical to mycosubtilin anteiso $C_{17}$ but with 14 more, including the intense y6 peak at 1029 instead of 1015 for all the other samples.

Fragments b less than b6 identical to anteiso $C_{17}$ mycosubtilin.

Fragments b greater than or equal to b6 identical to mycosubtilin but with 14 more.

These results show us that the molecule would be mycosubtilin with a $C_{18}$ rather than $C_{17}$ fatty acid.

On the basis of the order of elution of the various peaks, we deduce from this the existence of 5 novel forms of mycosubtilin: the forms Gln3, iso $C_{16}$, nC16, anteiso $C_{17}$, iso $C_{17}$ and a $C_{18}$ form. The correspondence of these forms with the ten peaks with the molecular masses of the molecules detected by the HPLC analysis of example 4.5 is presented in table 6 below:

TABLE 6

Correspondence between the masses of the 10 peaks detected by HPLC analysis and the mycosubtilin forms

| Peak n° | Mass | Form |
|---------|------|------|
| 1 | 1056 | $C_{16}$ |
| 2 | 1084 | iso$C_{16}$ GLN |
| 3 | 1084 | $_nC_{16}$ GLN |
| 4 | 1070 | iso$C_{16}$ |
| 5 | 1070 | $_nC_{16}$ |
| 6 | 1098 | anteisoI$C_{17}$ GLN |
| 7 | 1098 | iso$C_{17}$ GLN |
| 8 | 1084 | anteiso$C_{17}$ |
| 9 | 1084 | iso$C_{17}$ |
| 10 | 1098 | $C_{18}$ |

The formula of this novel $C_{18}$ mycosubtilin is as follows:

$$CH_3-(CH_2)_{14}-CH-CH_2-CO\text{-Asn-Tyr-Asn} \quad \text{(I)}$$
$$| \qquad\qquad\qquad |$$
$$NH-Asn-Ser-Pro-Gln$$

The formula of this novel $C_{17}$ Gln3 microsubtilin is as follows:

$$CH_3-(CH_2)_{13}-CH-CH_2-CO\text{-Asn-Tyr-Gln} \quad \text{(II)}$$
$$| \qquad\qquad\qquad |$$
$$NH-Asn-Ser-Pro-Gln$$

Example 5: Biological Activity of Various Isoforms of Mycosubtilin (MS) Vis-à-Vis Various Microorganisms Tests on antifungal activities were carried out by successive dilutions of the $C_{18}$ isoform ($C_{18}$ MS) in a liquid medium according to the protocol described in Besson et al. (Besson et al. 1979. Antifungal activity upon *Saccharomyces cerevisiae* of iturin A, mycosubtilin, bacillomycin L and of their derivatives; inhibition of this antifungal activity by lipid antagonists. J. Antibiot. (Tokyo) 32, 828-833) [19]. Cultures in 96-well microplates were carried out in a rich medium: glucose, 40 g/l; peptone, 10 g/l; yeast extract, 2 g/l; pH=7.2. Seeding of *Saccharomyces cerevisiae* was carried out at a $DO_{600nm}$ of 0.55 and the absorbance was read after 24 hours and the minimum inhibiting concentration (MIC) was then determined.

This experiment was also carried out with the following isoforms of mycosubtilin (MS): MS iso-$C_{16}$, MS n-$C_{16}$, MS anteiso-C17, MS iso-$C_{17}$. It was also carried out with a composition of mycosubtilins (MS comp.) comprising, as a percentage with respect to the weight of the composition, 26% of MS iso-$C_{16}$, 1% MS Gln3 $C_{17}$, 2% MS n-$C_{16}$, 44% MS anteiso-$C_{17}$, 23% MS iso-$C_{17}$ and 1% MS $C_{18}$.

This experiment was also carried out, for each of the aforementioned isoforms of mycosubtilins and composition on the following microorganisms: *Botrytis cinerea, Aspergillus niger, Sclerotinia sclerotium, Candida albicans*.

The MICs obtained for each of these experiments are presented in table 7 below:

TABLE 7

MIC of various isoforms of mycosubtilin and a composition vis-à-vis various microorganisms

| Micro-organisms | MIC (μM) | | | | |
|---|---|---|---|---|---|
| | MS iso-$C_{16}$ | MS n-$C_{16}$ | MS anteiso-$C_{17}$ | MS iso-$C_{17}$ | MS comp. |
| B. cinerea | 32 | 16 | 8 | 16 | 8 |
| A. niger | 32 | 16 | 8 | 16 | 8 |
| C. albicans | >32 | 8 | 32 | 16 | 8 |

These results show that the composition MS comp. has effects equivalent, or even superior, to the mycosubtilins currently used.

Example 6: Implementation of an Integrated Method for Producing, Extracting and Concentrating the Lipopeptides Produced by *B. subtilis* on Air/Liquid Membrane Contactor The description of this example refers to FIGS. 1 to 5.
In this example:
- the pumps P1, P2, P3, P4, P5, P6, P7, P8, P9, P10, P11, P12, P13 and P14 were Masterflex L/S peristaltic pumps compact drive model (Cole Parmer, Vernon Hills, Ill., U.S.A.),
- the pump P11 was of the N820.3 FT.18 type (KNF Neuberger Laboport, Freiburg, Germany),
- the valves V1, V4 and V5 were stop valves made from PTFE (W3250Y, Thermo Fisher Scientific, Roskilde, Germany),
- the valves V2, V3, V6 and V7 were three-way stop valves made from PTFE (W3250Z, Thermo Fisher Scientific, Roskilde, Germany),
- the tanks tank 2 and tank 4 were Nalgene tanks made from high-density polypropylene with a useful volume of 4 liters (2125-4000 Heavy Duty Bottles, Nalgene, Thermo Fisher Scientific, Roskilde, Germany),
- the tanks tank 1, tank 3, tank 5, tank 6 and tank 7 were Nalgene tanks made from high-density polypropylene with a useful volume of 10 or 20 liters (2250 Autoclavable Carboys, Nalgene, Thermo Fisher Scientific, Roskilde, Germany).
- the scales B1, B2, B3, B4, B5, B6 and B7 were of the CKW-55 type; Ohaus Corporation, Pine Brook, N.J., U.S.A.),
- the strain of *Bacillus subtilis* was the strain *B. subtilis* BBG125.

6.1 Environmental Conditions and Sensors Used for the Culture

Unless indicated to the contrary, the pH was regulated to 7+/−0.1 by means of the controlled addition, respectively by the pumps P2 and P3, of solutions of 0.66M $H_3PO_4$ or 3M NaOH sterilised previously by autoclaving at 121° C. for 20 minutes.

A pH electrode was calibrated before autoclaving of the tank using commercial solutions buffered to pH 4.0 and pH 7.0 and stored at 4° C. The process was conducted at 22°+/−0.1° C. by means of an Alpha Laval 1 $m^2$ tubular heat exchanger (104878, Alpha Laval Corporate AB, Lund, Sweden). The concentration of dissolved oxygen $pO_2$ was measured by means of an oxygen sensor (Mettler Toledo, Viroflay, France). The electrolyte of the oxygen sensor was renewed at each experiment. The oxygen sensor was calibrated after autoclaving of the tank when the culture medium reached the set temperature and pH of the experiment. The 0% of $pO_2$ was obtained by connecting the cable of the sensor to earth and the 100% $pO_2$ by saturating the medium with air (1000 rpm and 1 vvm).

The aeration rate (Fe) was fixed at 0.25 volumes of air per volume of liquid per minute (vvm), that is to say 0.75 liters/min for 3 liters of Landy medium (example 2.1). The incoming air was filtered through a 0.2 sterilising filter.

The software used for controlling the process and acquiring the data was AFS Biocommand (New Brunswick Scientific, Edison, N.J., U.S.A.). The purity of the culture was checked after 48 hours and at the end of culture. Culture samples of 10 ml were regularly taken and centrifuged, the optical density and the dry weight were determined, and the supernatant was stored before analysis. The incoming and outgoing gases were analysed in order to obtain data on the respiration of the microorganism. A paramagnetic sensor made it possible to analyse the quantity of oxygen and an infrared sensor that of the carbon dioxide (Xentra 4400; Servomex Company Inc., Sugar Land, Tex., U.S.A.). The analyser was integrated in a multiplexed device that afforded a sequential analysis on six channels, drying of the gases on Naflon membrane (Permapur, Saint-Leonard, Quebec) and automatic calibration.

6.2 the Air/Liquid Membrane Contactor

The air/liquid membrane contactor M1 used in this example is supplied by GE-Healthcare, reference CFP-6-D-45 (GE-Healthcare Europe GmbH, Munich, Germany). It consists of an external module comprising two compartments C1 and C2. In compartment C1, a sterile gas circulates containing oxygen. In compartment C2, the culture medium containing the inoculum circulates at a rate of 24 liters/h/$m^2$ of membrane imposed by the pump P4.

The membrane M1 has a surface area of 2.5 $m^2$ and is sterilised before use by autoclaving at 121° C. for 20 minutes (this criterion is not exhaustive). The membrane consists of a set of hollow polyethersulfone fibres having a porosity of 0.65 μm.

6.3. Device for Continuous Culture of *Bacillus subtilis*: Coupling of a System for Extraction/Concentration of the Biosurfactants by Air/Liquid Membrane Contactor 6.3.1. Coupling of a System for Extraction/Concentration of the Lipopeptides with the Air/Liquid Membrane Contactor.

The device used for the continuous culture of *B. subtilis* comprises an air/liquid membrane contactor M1 made from hollow fibres in which *B. subtilis* BBG125 has been cultivated in a Landy medium. *B. subtilis* BBG125 immobilised on the surface of the membrane M1 degrades this substrate by excreting biosurfactants. The device also comprises means for supplying and drawing off a given flow rate of said substrate continuously in the production device comprising the membrane M1.

The membrane M1 provides, in a sterile environment, the oxygen necessary for the growth of the microorganism in the culture medium, by means of the diffusion of oxygen through its pores.

A peristaltic pump P1 continuously supplies the membrane M1, at a rate F1, with fresh Landy medium stored in a tank 1, and likewise a peristaltic pump P5 continuously draws off the culture medium from the production device comprising the membrane M1 described above at a rate F2.

The inoculum and the fermentation conditions remain equivalent to those described previously. In order to keep the environment sterile, all the constituents of the device and the various membranes used were sterilised at 121° C. for 20 minutes.

One feature of this device stems from the fact that it is possible to recycle or not, in the production device comprising the membrane M1, all the microorganisms cells after having removed from them the residues of organic matter and biosurfactants, which makes it possible to obtain a high rate of growth of the microorganisms in the production device.

Moreover, this device enables oxygen to be diffused in the culture medium without the formation of bubbles or foam.

6.3.2. Extraction of the Lipopeptides and Recycling of the Cells by Microfiltration The device described previously is therefore characterised by the fact that it comprises tangential microfiltration and ultrafiltration means, situated at the discharge from the production device, which separate the liquid into several fractions.

A first microfiltration step was performed on a membrane M2 made from hollow polyethersulfone fibres with a pore size of 0.2 μm (GE Healthcare) with a surface area of 0.4 m$^2$, in which the culture medium containing the cells circulates, by means of the volumetric pump P4 described above, in the compartment C3 of the membrane M2 referred to as the residue. Under the effect of a volumetric pump P5, the medium passes by tangential filtration through the pores of the membrane M2 to the compartment C4 of the membrane M2. By this means, the culture medium containing the biosurfactants has the cells removed and is extracted and then collected in a tank 2 stirred by blades driven by a motor B or by magnetic agitation (magnetic agitator, W10512, Thermo Fisher Scientific, Roskilde, Germany) at a speed of 160 rpm.

The culture medium of the production device comprising the membrane M1 is taken off continuously to the tank 2. In order to compensate for this drawing off and to keep a constant volume in the membrane M1, the pump P1 supplies the bioreactor with new medium contained in tank 1.

Moreover, tank 2 and tank 3 are placed respectively on scales B2 and B3. It is the latter that control the output of the peristaltic pump P1 (CKW-55; Ohaus Corporation, Pine Brook, U.S.A.), making it possible to maintain a constant volume inside the membrane M1 and thereby obtaining F1=F2. In each of the experiments carried out, the degree of dilution is changed after the passage of at least four air/liquid membrane contactor volumes comprising the membrane M1.

The outputs of the pumps P1 and P5 are equal and adjusted so as to obtain, in the device comprising the membrane M1, a degree of dilution of 0.1 h$^{-1}$, that is to say an hourly flow rate equal to 0.1 times the volume of the aqueous phase contained in the production device comprising the membrane M1.

A variant of this method has also been implemented. It consists of recycling or not the cells inside the membrane M1. It is then an open continuous mode presented in broken lines in FIGS. 3 and 4. In the case of non-recycling by the set of valves V6, V7 and V8, the culture medium can be pumped by the pump P13 from the membrane M1 and collected in the tank 7. A drain valve makes it possible to eliminate the cell concentrate intermittently. In this case, the step of microfiltration by the membrane M1 is performed directly on the medium contained in the tank 7 and the cells are then concentrated in the tank 7 rather than in the production device comprising the membrane M1.

6.3.3. Concentration of the Lipopeptides by Ultrafiltration

The filtrate contained in the tank 2 is finally driven, by means of a pump P6, into the compartment C5 of a stainless steel tangential ultrafiltration system (Sartocon 2 plus, 17546—-202, Sartorius, Gottingen, Germany), comprising an ultrafiltration membrane M3 with a cutoff threshold of 10 kDa made from regenerated cellulose (Hydrosart Ultrafilter, 3021443930E-BSW, Sartorius, Gottingen, Germany). Above the critical micell concentration, the biosurfactants are concentrated in the compartment C5, referred to a residue, and thus return to the tank 2. The culture medium is extracted, under the control of a pump P7, at a rate equivalent to that of the pump P5, to a compartment C6, called ultrafiltrate, and collected in a tank 3. The flow rate will depend on the flow rate imposed by the pump P7 and regulated by means of the information collected by the various scales B2, B3 and B4.

6.4. Purification of the Lipopeptides 6.4.1. Purification by Ultrafiltration/Diafiltration The purification of the lipopeptides presented in this example is based on the concatenation of ultrafiltration steps through a stainless steel tangential ultrafiltration system (Sartocon 2 plus, 17546—-202, Sartorius, Gottingen, Germany), comprising an ultrafiltration membrane M4 with a cutoff threshold of 10 kDa made from regenerated cellulose (Hydrosart Ultrafilter, 3021443930E-BSW, Sartorius, Gottingen, Germany). This step aims to eliminate from the culture broth a major part of the residual substances such as glucose, glutamate and the various primary metabolites. The formation of micells and micell complexes by the mycosubtilin, when it is situated above its CMC, makes it possible to retain it and therefore concentrate it in the residue, by virtue of the use of the ultrafiltration membrane M4.

This step is performed at 25° C. and at a pressure of 0.5 bar. This purification step is performed on the concentrated lipopeptides in the tank 2. After opening of the valve V1, the pump P8 drives the concentrate to the tank 4 (Nalgene, made from high-density polypropylene with a useful volume of 4 liters (2125-4000 Heavy Duty Bottles, Nalgene, Thermo Fisher Scientific, Roskilde, Germany)) stirred by blades driven by a motor C or by magnetic agitation (magnetic agitator, W10512, Thermo Fisher Scientific, Roskilde, Germany) identical to the motor B.

The following steps are performed sequentially:

Ultrafiltration: The concentrate is transferred into the tank 4, under the control of a Masterflex L/S peristaltic pump P8 compact drive model (Cole Parmer, Vernon Hills, Ill., U.S.A.), and then purified on the membrane M4, under the control of a Masterflex L/S peristaltic pump P9 compact drive model (Cole Parmer, Vernon Hills, Ill., U.S.A.) and collected in the tank 4. The Masterflex L/S peristaltic pump P10 compact drive model (Cole Parmer, Vernon Hills, Ill., U.S.A.) makes it possible to pass the remainder of the constituents of the medium to the compartment C8 and the tank 5 (Nalgene made from high-density polypropylene with a useful volume of 10 or 20 liters (2250 Autoclavable Carboys, Nalgene, Thermo Fisher Scientific, Roskilde, Germany)). This process is continued until the volume contained in the tank 4 is reduced to 10% of the volume initially in the tank 4.

Diafiltration: This step dilutes the culture broth in order to facilitate the passage of the residual substances through the ultrafiltration membrane M4. The water is then added to the tank 4 by opening the valve V2 until the volume in the tank 4 regains its original level. There follows an ultrafiltration step as described above. This diafiltration step is performed four times in succession.

Ultrafiltration in the presence of methanol (MeOH): Following the diafiltration steps, MeOH is added from the tank 6 (Nalgene made from high-density polypropylene with a useful volume of 10 or 20 liters (2250 Autoclavable Carboys, Nalgene, Thermo Fisher Scientific, Roskilde, Germany) to the tank 4 via the Masterflex L/S peristaltic pump P12 compact drive model (Cole Parmer, Vernon Hills, Ill., U.S.A.) and the valve V2. This addition of MeOH is controlled by the scales B4, B5 and B6 so that the solution present at this time in the tank 4 contains 70% MeOH (v/v). There follows an ultrafiltration step as described above. This step will destroy the micells and pass the mycosubtilin monomers through the pores of the membrane M4.

After filtration, a solution consisting of mycosubtilin and 70% methanol is collected on the ultrafiltrate side, but this time the ultrafiltrate is collected in the vessel of a Rotavapor VV2000 evaporator (Evapo) (Heidolph Instruments GmbH & Co., Schwabach, Germany) by means of the set of valves V3 and V4.

At the end of each step, samples are taken on the filtrate side and the residue side. Thus the balance of the purification can be established. This makes it possible to determine the mycosubtilin losses caused by the ultrafiltration and diafiltration steps, by calculating the ratio of the quantity of concentrated mycosubtilin obtained after ultrafiltration to the quantity of mycosubtilin initially present in the tank 4. The yield of these steps is greater than 70%.

6.4.2. Concentration of the Lipopeptides by Evaporation

The evaporator (Evapo) concentrates the mycosubtilins by removing all the methanol and some of the water. This evaporation takes place at a residual pressure of 50 mbar imposed by the vacuum pump P11, type N820.3 FT.18 (KNF Neuberger Laboport, Freiburg, Germany) and at 50° C. During this step, the methanol is evaporated and its vapours are condensed by means of the condenser, and is recycled in the tank 6.

6.4.3. Freeze Drying of the Lipopeptides

An optional freeze drying step was added to this method in order to improve the preservation of the product. The freeze drying of the lipopeptides is performed directly using a concentrated solution X issuing from the evaporation and recovered by the valve V5. This is first of all frozen at −20° C. and then freeze dried by means of a Heto Power Dry PL 9000 freeze dryer (Jouan Nordic, Allerod, Denmark), in accordance with the following steps: 1 hour at −30° C.; 5 hours at −10° C.; 5 hours at 0° C.; 5 hours at −20° C.; 5 hours at 35° C. The freeze drying was carried out at a residual pressure of 15 mbar.

Example 7: Washing of the Membranes and Recovery of the Lipopeptides

Because of the affinity of the lipopeptides for the interfaces, the protocol for washing the membranes was studied and optimised. It takes account of the nature of the membranes and is in agreement with the recent work published on this subject (Chen, Chen and Juang, 2007. Separation of surfactin from fermentation broths by acid precipitation and two-stage dead-end ultrafiltration processes. J. Membr. Sci. 299, 114-121 [20]; Chen, Chen, and Juang, 2008. Flux decline and membrane cleaning in cross-flow ultrafiltration of treated fermentation broths for surfactin recovery. Sep. Purif. Technol. 62, 47-55 [21]). These washings denature neither the lipopeptides nor the membranes. The use of solvents is proscribed although some, such as methanol, are very effective for detaching the lipopeptides. Tests for sensitivity to pH determined that a pH=10 is the limit of degradability of the lipopeptides. The washings are performed under stirring and fermentation conditions. The protocol is implemented in seven water-based washing steps.

Two washings were performed with 3 liters of distilled water at 30° C. for 30 minutes. These detached the slightly immobilised biomass.

The second washing with distilled water at 30° C. made it possible to measure the oxygen transfer coefficient.

Two washings were performed with 3 liters of 0.1 M NaOH at 50° C. for 1 hour. These detached the highly immobilised biomass and desorbed the majority of the lipopeptides.

The membrane was then regenerated with a 0.5 M solution of NaOH at 50° C. for 1 hour then with a 100 ppm solution of NaOCl at 50° C. for 1 hour, and was then cleaned with distilled water at 25° C. until neutrality was achieved in the membrane.

The whole of the aforementioned method was also implemented by duplicating each membrane, so that it can be washed and regenerated sequentially. This made it possible to implement the method without discontinuing. In order to implement this alternative method, tanks (not shown) containing the 0.1 and 0.5 M soda solution were added to the device.

Example 8: Quantification of the Biosurfactants Produced

In this example, several tests were performed to produce biosurfactants by B. subtilis by fermentation of glucose at a concentration of 20 g/l, in a production device containing 3 liters of culture medium and a total surface area of air/liquid membrane contactor of 2.5 m$^2$, conforming to the air/liquid membrane contactor described in example 6. Each of the experiments was repeated twice. Only the average of these doublets is presented below. The standard deviation is between 5% and 15%.

The experimentation conditions were adjusted as follows:
the pH was maintained at 7,
the air flow in the air/liquid membrane contactor was 1 vvm,
the culture medium volume was 3 liters circulating in the fibres of said membrane at a speed of 0.021 m/s,
the pressure of the whole of the system was atmospheric pressure, except at the air inlet, this may be slightly above atmospheric pressure at 0.4 bar,
the oxygenation conditions of the culture medium were fixed with a volumetric oxygen transfer coefficient of around 40 $h^{-1}$.

Chromatographic analysis by HPLC quantified the substrates and biosurfactants in the various tanks.

Analysis of the oxygen consumed made it possible to determine the quantity of cells immobilised on the membrane.

The following formula was used to determine the biomass immobilised on the membrane over time in (g $m^{-2}$) considering that the free and immobilised cells have different specific oxygen consumption rates, oxygen being more accessible for the cells immobilised on the membrane than for those in suspension:

biomass immobilized on the membrane at a given time in (g $m^{-2}$)=(OUR-($X$*$OUR_{spec\ ci}$))*$V$/($OUR_{spe\ ci}$*$a$)

in which:
OUR=oxygen consumption rate
$OUR_{spe\ ci}$=specific oxygen consumption rate of the free cells
$OUR_{spe\ ci}$=specific oxygen consumption rate of the immobilised cells
V=reaction volume
X=concentration of free biomass
a=surface area of the membrane The steps of washing the membranes described in these examples were performed in accordance with the method described in example 7.

8.1 Production of Mycosubtilin by *B. subtilis* BBG125, Batch Mode

In this example, the *B. subtilis* BBG125 strain was cultivated in batches at 30° C. for 48 hours in an air/liquid membrane contactor M1.

8.1.1 Analysis of the Biomass Produced.

In this method two types of biomass were observed, one in free suspension in the culture medium and the other immobilised on the air/liquid membrane contactor.

The free cells were cultivated exponentially at 0.2 $h^{-1}$ of specific growth rate up to the $18^{th}$ hour. The free biomass reached a maximum of 2.6 g $l^{-1}$ after one day of culture and then remained constant until the end of the culture.

Analysis of the gases revealed the presence of a biomass immobilised on the membrane. The growth of this biomass took place during the first day of culture in order to attain 1.2 g $m^{-2}$. A glucose consumption rate of 1.61 g $l^{-1}$ h was measured during the first day of culture, and then this decreased as the glucose was depleted in the medium.

8.1.2 Analysis of the Mycosubtilin Produced

The production of mycosubtilin reached 10 mg $l^{-1}$ after two days of culture. 45 mg was desorbed during washing of the membrane resulting in a total production of 25 mg $l^{-1}$ and a mean productivity of 0.5 mg $l^{-1}$ $h^{-1}$. After purification by the microfiltration, ultrafiltration/diafiltration and drying steps, a mixture of mycosubtilin in powder form containing the novel forms of mycosubtilin was obtained. The purity of this mixture was more than 94%.

8.2 Continuous Production, Extraction and Purification of Mycosubtilin by *B. subtilis* BBG125 with Completely Recycled Cells In this example, the *B. subtilis* BBG125 strain (filed on 10 Mar. 2011 under the number CNCM 1-4451 at the National Collection of Microorganism Cultures (CNCM) of the Institut Pasteur (Paris, France)), capable of producing only mycosubtilin in a constitutive manner, was cultivated continuously at 22° C. for 72 hours in an air/liquid membrane contactor M1.

In addition to the air/liquid membrane contactor that allows the growth and immobilisation of the cells, the method presented in this example is also characterised by the presence of:
devices for supplying and drawing off continuously in said reactor a given flow of said substrate, in accordance with those described in example 6,
a microfiltration membrane M2 with a surface area of 0.45 $m^2$ and a pore size of 0.2 in accordance with that described in example 6,
three tanks: supply (tank 1), concentration (tank 2) and waste (tank 3), in accordance with those described in example 6, and
an ultrafiltration membrane M3 with a surface area of 0.1 $m^2$ and a cutoff threshold of 10 kDa, in accordance with that described in example 6.

In addition, the supply and drawing-off rates of the pumps P1 and P5 in accordance with those described in this example were equal and adjusted so as to obtain a degree of dilution of around 0.1 $h^{-1}$, that is to say an hourly rate equal to 0.1 times the volume of the aqueous phase contained in the production device.

One feature of this method in accordance with the present invention lies in the fact that all the microorganism cells in the production device are recycled after they have had the residues of organic matter and biosurfactants removed, which makes it possible to obtain a high growth rate of the microorganisms on the membrane. The continuous culture was preceded by 20 hours of batch culture.

8.2.1 Analysis of the Biomass

During the first 40 hours of the continuous culture at 0.1 h of degree of dilution, the free biomass continued to increase in the broth up to 7.2 g $l^{-1}$. Next, its concentration remained constant, which certainly revealed the presence of an inhibiter. On the other hand, analysis of the gases revealed a significant immobilisation of the cells on the membrane, which reached 3.1 g $m^{-2}$ after three days of culture. During the first two days of culture, the concentration of glucose decreased with a glucose consumption rate of 1.5 g $l^{-1}$ $h^{-1}$.

8.2.2 Analysis of the Surfactin Produced

The mycosubtilin was thus extracted through the microfiltration membrane and was indeed concentrated by the 10 kDa ultrafiltration membrane; the accumulation thereof in the intermediate tank was observed. The mycosubtilin productivity increased in the course of the first 40 hours of culture and reached a maximum of 1.5 mg $l^{-1}$ $h^{-1}$. After this experiment, washing of the membranes recovered 84 mg of mycosubtilin. At the end of this experiment, the continuous culture produced 895 mg of mycosubtilin in solution, that is to say an average concentration produced of 48 mg of mycosubtilin produced per liter of medium consumed. The ultrafiltration/diafiltration steps obtained surfactin in solution with a purity of 90%. This continuous method shows a productivity three times greater than that obtained with the batch mode described in example 8.1.

LIST OF REFERENCES

[1] Ongena, M. and Jacques, P. 2008. *Bacillus* lipopeptides: versatile weapons for plant disease biocontrol. Trends Microbiol. 16, 115-125.
[2] CZ 20011620
[3] DE 102005050123
[4] FR 2578552
[5] Guez, J. S. et al., 2007. Setting up and modelling of overflowing fed-batch cultures of *Bacillus subtilis* for the production and continuous removal of lipopeptides, J. Biotechnol., 131, 67-75.
[6] Davis, D. A., Lynch, H. C. and Varley, J., 1999. The production of Surfactin in batch culture by *Bacillus subtilis* ATCC 21332 is strongly influenced by the conditions of nitrogen metabolism. Enzyme Microb. Technol. 25, 322-329.
[7] WO 0226961
[8] EP 1320595
[9] Landy, M. et al. 1948. Bacillomycin; an antibiotic from *Bacillus subtilis* active against pathogenic fungi. Proc. Soc. Exp. Biol. Med. 67, 539-541.
[10] Guez, J. S. et al., 2008. Respiration activity monitoring system (RAMOS), an efficient tool to study the influence of the oxygen transfer rate on the synthesis of lipopeptide by *Bacillus subtilis*. J. Biotechnol. 134, 121-126.
[11] Remize, P. J. and Cabassud, C. 2003. A novel bubble-free oxidation reactor: the G/L membrane contactor. Recent progress in process engineering. Integration of membranes in the processes 2. Lavoisier Tec et Doc.
[12] Duitman, E. H. et al., 1999. The mycosubtilin synthetase of *Bacillus subtilis* ATCC 6633: a multifunctional hybrid between a peptide synthetase, an amino transferase, and a fatty acid synthase. Proc. Natl. Acad. Sci. U.S.A., 96, 13294-13299.
[13] Leclére, V. et al., 2005. Mycosubtilin overproduction by *Bacillus subtilis* BBG100 enhances the organism's antagonistic and biocontrol activities. Appl. Environ. Microbiol. 71, 4577-4584.
[14] Sambrook, J. and Russell, D. W. 2001. Molecular cloning: a laboratory manual, $3^{rd}$ ed., Cold Spring Harbor Laboratory, Cold Spring Harbor, N.Y.
[15] Dennis, J. J. and Zylstra, G. J. 1998. Plasposons: modular self-cloning minitransposon derivatives for rapid genetic analysis of gram-negative bacterial genomes. Appl. Environ. Microbiol. 64, 2710-2715.
[16] Herrero, M., de Lorenzo, V., and Timmis, K. N. 1990. Transposon vectors containing non-antibiotic resistance selection markers for cloning and stable chromosomal insertion of foreign genes in gram-negative bacteria, J. Bacteriol. 172, 6557-6567.
[17] Bertani, G. 2004. Lysogeny at mid-twentieth century: P1, P2, and other experimental systems. J. Bacteriol. 186, 595-600.
[18] Dubnau, D. A. 1982. Genetic transformation of *bacillus subtilis* p148-178. In D. A. Dubnau (Ed) The molecular biology of the Bacilli, vol I. *Bacillus subtilis*. Academic Press, Inc. New York.
[19] Besson, F. et al. 1979. Antifungal activity upon *Saccharomyces cerevisiae* of iturin A, mycosubtilin, bacillomycin L and of their derivatives; inhibition of this antifungal activity by lipid antagonists. J. Antibiot. (Tokyo) 32, 828-833.
[20] Chen, H. L., Chen, Y. S., and Juang, R. S. 2007. Separation of surfactin from fermentation broths by acid precipitation and two-stage dead-end ultrafiltration processes. J. Membr. Sci. 299, 114-121.
[21] Chen, H. L., Chen, Y. S., and Juang, R. S. 2008. Flux decline and membrane cleaning in cross-flow ultrafiltration of treated fermentation broths for surfactin recovery. Sep. Purif. Technol. 62, 47-55.

The invention claimed is:

1. A composition comprising: a mycosubtilin, the fatty acid chain of which comprises 17 carbon atoms and which has glutamine in place of asparagine in position 3 in its peptide cycle (C17 Gln3 mycosubtilin), represented by the following formula (II):

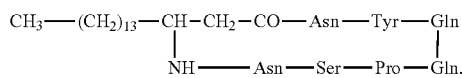

2. The composition of claim 1, further comprising at least one mycosubtilin chosen from the group consisting of an iso-C16 mycosubtilin, an n-C16 mycosubtilin, an anteiso-C17 mycosubtilin, an iso-C17 mycosubtilin, and mixtures thereof.

3. An antifungal composition comprising:
   a mycosubtilin, the fatty acid chain of which comprises 17 carbon atoms and which has glutamine in place of asparagine in position 3 in its peptide cycle (C17 Gln3 mycosubtilin), represented by the following formula (II):

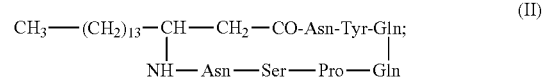

and one or both of:
(i) a mycosubtilin, the fatty acid chain of which comprises 18 carbon atoms (C18 mycosubtilin), represented by the following formula (I):

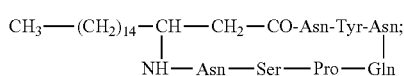

or
(ii) at least one mycosubtilin chosen from the group consisting of an iso-C16 mycosubtilin, an n-C16 mycosubtilin, an anteiso-C17 mycosubtilin, an iso-C17 mycosubtilin, and mixtures thereof.

4. The antifungal composition of claim 3, comprising: between 1% and 20% of the C17 Gln3 mycosubtilin; and one or more of:

between 1% and 60% of iso-C16 mycosubtilin;
between 1% and 10% of n-C16 mycosubtilin;
between 20% and 95% of anteiso-C17 mycosubtilin;
between 5% and 30% of iso-C17 mycosubtilin; and
between 1% and 5% of C18 mycosubtilin.

5. The antifungal composition of claim 4, comprising between 1% and 20% of C17 Gln3 mycosubtilin, between 1% and 60% of iso-16 mycosubtilin, between 1% and 10% of n-C16 mycosubtilin, between 20% and 95% of anteiso-C17 mycosubtilin, between 5% and 30% of iso-C17 mycosubtilin, and between 1% and 5% of C18 mycosubtilin.

* * * * *